US012766137B2

(12) United States Patent
Jia et al.

(10) Patent No.: US 12,766,137 B2
(45) Date of Patent: Oct. 20, 2026

(54) SALT TYPES OF TRICYCLIC TETRAHYDRO ISOQUINOLINE DERIVATIVE

(71) Applicants: JIANGSU HENGRUI PHARMACEUTICALS CO., LTD., Lianyungang (CN); SHANGHAI HENGRUI PHARMACEUTICAL CO., LTD., Shanghai (CN)

(72) Inventors: Lina Jia, Lianyungang (CN); Lin Wang, Lianyungang (CN); Qiyun Shao, Shanghai (CN); Jun Feng, Shanghai (CN); Junran Yang, Lianyungang (CN); Zhenxing Du, Lianyungang (CN)

(73) Assignees: JIANGSU HENGRUI PHARMACEUTICALS CO., LTD., Lianyungang (CN); SHANGHAI HENGRUI PHARMACEUTICAL CO., LTD., Shanghai (CN)

( * ) Notice: Subject to any disclaimer, the term of this patent is extended or adjusted under 35 U.S.C. 154(b) by 358 days.

(21) Appl. No.: 18/576,806

(22) PCT Filed: Jul. 8, 2022

(86) PCT No.: PCT/CN2022/104669
§ 371 (c)(1),
(2) Date: Jan. 5, 2024

(87) PCT Pub. No.: WO2023/280309
PCT Pub. Date: Jan. 12, 2023

(65) Prior Publication Data

US 2024/0374581 A1 Nov. 14, 2024

(30) Foreign Application Priority Data

Jul. 9, 2021 (CN) ......................... 202110779905.3

(51) Int. Cl.
*A61K 31/4725* (2006.01)
*A61P 35/00* (2006.01)

(52) U.S. Cl.
CPC .......... *A61K 31/4725* (2013.01); *A61P 35/00* (2018.01)

(58) Field of Classification Search
CPC ............................ A61K 31/4725; A61P 35/00
See application file for complete search history.

(56) References Cited

U.S. PATENT DOCUMENTS

| | | | |
|---|---|---|---|
| 2016/0068542 A1 | 3/2016 | Shi et al. |
| 2017/0320871 A1 | 11/2017 | Labadie et al. |
| 2022/0098195 A1 | 3/2022 | Liu |

FOREIGN PATENT DOCUMENTS

| | | | |
|---|---|---|---|
| CN | 109219604 A | 1/2019 |
| CN | 109776523 A | 5/2019 |
| EP | 1113007 A1 | 7/2001 |
| WO | 2014106848 A1 | 7/2014 |
| WO | 2014135834 A1 | 9/2014 |
| WO | 2014141292 A2 | 9/2014 |
| WO | 2014151899 A1 | 9/2014 |
| WO | 2014165723 A2 | 10/2014 |
| WO | 2014191726 A1 | 12/2014 |
| WO | 2015092634 A1 | 6/2015 |
| WO | 2016202161 A1 | 12/2016 |
| WO | 2019228443 A1 | 12/2019 |
| WO | 2021139756 A1 | 7/2021 |

OTHER PUBLICATIONS

Scott James S. et al: "Discovery of AZD9833, a Potent and Orally Bioavailable Selective Estrogen Receptor Degrader and Antagonist", Journal of Medicinal Chemistry, vol. 63, No. 23, Dec 10, 2020 (Dec 10, 2020), pp. 14530-14559, XP055823030, US ISSN: 0022-2623, DOI: 10.1021/acs.jmedchem.0c01163.

Hilfiker R., Blatter F, van Raumer M.: "Relevance of Solid-state Properties for Pharmaceutical products" In: Hilfiker, R.: "Polymorphism in the Pharmaceutical Industry", Jan. 2006 (Jan. 2006), Wiley-VCH, Weinheim, XP002528052, ISBN: 78-3-527-31146-0 pp. 1-19, pp. 7-14, paragraph 1.4.

(Continued)

*Primary Examiner* — Kamal A Saeed
(74) *Attorney, Agent, or Firm* — Harness, Dickey & Pierce, P.L.C.

(57) ABSTRACT

The present disclosure relates to salt types of a tricyclic tetrahydro isoquinoline derivative. Specifically, the present disclosure relates to different salt types of a compound as represented by formula (I) and a preparation method therefor. The salt types of the compound of formula (I) provided in the present disclosure have good stability and can be better used for clinical treatment.

(I)

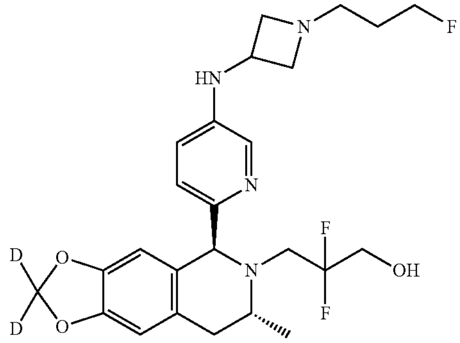

26 Claims, 9 Drawing Sheets

Specification includes a Sequence Listing.

(56) References Cited

OTHER PUBLICATIONS

International Search Report (English and Chinese) and Written Opinion of the ISA (Chinese) issued in PCT/CN2022/104669, mailed Oct. 10, 2022; ISA/CN.

Toba, et al., Synthesis and evaluation of N-(4-benzylphenyl) piperazines as VGF inducers, Bioorganic & Medicinal Chemistry Letters, 2018, 28(14), 2528-2532.

SALT TYPES OF TRICYCLIC TETRAHYDRO ISOQUINOLINE DERIVATIVE

CROSS-REFERENCE TO RELATED APPLICATIONS

The present application is a U.S. National Phase Application under 35 U.S.C. 371 of International Application No. PCT/CN2022/104669 filed on Jul. 8, 2022, which claims priority to the Chinese Patent Application No. 2021107799053 filed on Jul. 9, 2021, which is incorporated herein by reference in its entirety.

SEQUENCE LISTING

This application contains references to amino acid sequences and/or nucleic acid sequences which have been submitted concurrently herewith as the sequence listing text file entitled "000190usnp_SequenceListing.XML", file size 3,213 bytes, created on Dec. 27, 2023. The aforementioned sequence listing is hereby incorporated by reference in its entirety pursuant to 37 C.F.R. § 1.52(e)(5).

TECHNICAL FIELD

The present disclosure relates to a salt form of a tricyclic tetrahydroisoquinoline derivative, a preparation method therefor, and medical use thereof, and belongs to the field of pharmacy.

BACKGROUND

Fulvestrant in CSCO guidelines for breast cancer diagnosis and treatment (2020 edition) was adjusted to be a class I recommendation to treat endocrine therapy-naive hormone receptor-positive advanced breast cancer patients, and fulvestrant+CDK4/6 inhibitor was added as a class II recommendation; in addition, a combination of fulvestrant and the CDK4/6 inhibitor has become a class I recommendation for patients after nonsteroidal AI (NSAI) and steroidal AI (SAI) treatment failures. As the only approved SERD at present, fulvestrant was approved as an injection, which is inconvenient for patients to take. Therefore, the search for a new and more effective SERD not only has great market value, but also brings medication selectivity and convenience for breast cancer patients. SAI439859 from Sanofi is currently in clinical phase III as a new generation of orally available SERD inhibitors; in addition, GDC-9545 from Roche, AZD-9833 from Astrazeneca, and RAD1901 from Radius have all been subjected to phase III. Disclosed patent applications regarding selective estrogen receptor-mediated modulators include WO2014165723, WO2014151899, WO2014141292, WO2014191726, WO2015092634, WO2014135834, WO2014106848, and EP1113007.

PCT application No. WO2021139756A discloses a tricyclic tetrahydroisoquinoline derivative of formula (I) used for a selective estrogen receptor degrader (SERD), which is necessary for the research on a salt and a crystal form thereof in order to meet the requirement of medication, (I)

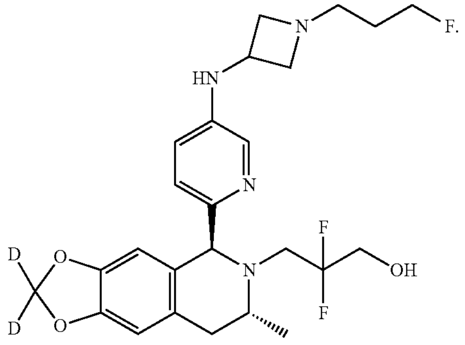

SUMMARY

The present disclosure provides a pharmaceutically acceptable salt of a compound of formula (I), and the pharmaceutically acceptable salt is selected from the group consisting of phosphate, sulfate, tartrate, citrate, hydrochloride, hydrobromide, mesylate, formate, acetate, succinate, maleate, malate, and p-toluenesulfonate, (I)

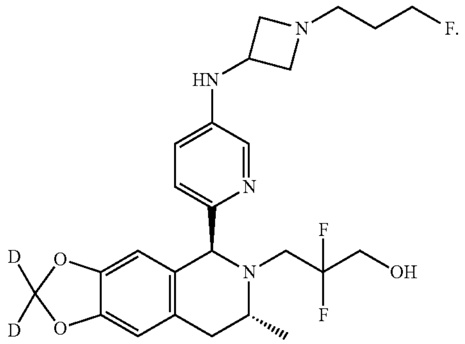

In some embodiments, in the pharmaceutically acceptable salt of the compound of formula (I) provided in the present disclosure, the compound of formula (I) and an acid molecule are in an amount-of-substance ratio selected from the group consisting of 1:5 to 5:1.

In some embodiments, in the pharmaceutically acceptable salt of the compound of formula (I) provided in the present disclosure, the compound of formula (I) and the acid molecule are in an amount-of-substance ratio of 1:1.

In some embodiments, in the pharmaceutically acceptable salt of the compound of formula (I) provided in the present disclosure, the compound of formula (I) and the acid molecule are in an amount-of-substance ratio of 1:3.

In some embodiments, the present disclosure provides a phosphate of the compound of formula (I), wherein the compound of formula (I) and a phosphoric acid molecule are in an amount-of-substance ratio of 1:3.

The present disclosure provides a crystal form I of the phosphate of the compound of formula (I), wherein the compound of formula (I) and the phosphoric acid molecule are in an amount-of-substance ratio of 1:3, and in an X-ray powder diffraction pattern, the crystal form has characteristic peaks at 2θ angles of diffraction of 6.1, 13.5, 19.2, and 22.3.

In some embodiments, the crystal form I of the phosphate of the compound of formula (I) comprises the compound of formula (I) and the phosphoric acid molecule in an amount-of-substance ratio of 1:3, and, in the X-ray powder diffraction pattern, has characteristic peaks at 2θ angles of diffraction of 6.1, 13.5, 13.9, 19.2, 21.8, 22.3, and 23.4.

In some embodiments, the crystal form I of the phosphate of the compound of formula (I) comprises the compound of formula (I) and the phosphoric acid molecule in an amount-of-substance ratio of 1:3, and, in the X-ray powder diffraction pattern, has characteristic peaks at 2θ angles of diffraction of 6.1, 12.4, 13.5, 13.9, 15.0, 16.3, 16.9, 19.2, 20.8, 21.8, 22.3, 23.4, 24.1, 24.6, 26.2, 27.5, and 30.0.

In some embodiments, the crystal form I of the phosphate of the compound of formula (I) comprises the compound of formula (I) and the phosphoric acid molecule in an amount-of-substance ratio of 1:3, and the X-ray powder diffraction pattern at 2θ angles of diffraction is shown in FIG. 2.

In some embodiments, the crystal form I of the phosphate of the compound of formula (I) comprises the compound of formula (I) and the phosphoric acid molecule in an amount-of-substance ratio of 1:3, and belongs to a triclinic system with axial lengths a=8.0475 (3) Å; b=8.0903 (3) Å; c=84.695 (4) Å; axial angles α=89.575 (2)°; β=89.859 (2)°; γ=60.745 (2)°; and a unit cell volume V=4810.7 (3) $Å^3$.

The present disclosure provides a method for preparing the phosphate of the compound of formula (I) or the crystal form I of the phosphate of the compound of formula (I), comprising the step of reacting the compound of formula (I) with phosphoric acid.

The present disclosure provides a method for preparing the crystal form I of the phosphate of the compound of formula (I), comprising the following steps:

1) preparing a solution of the compound of formula (I) in a solvent A, wherein the solvent A is selected from the group consisting of a ketone solvent, an ester solvent, and an ether solvent;
2) preparing a solution of phosphoric acid in a solvent B, wherein the solvent B is selected from the group consisting of water and an alcohol solvent; and
3) mixing the solution of the compound of formula (I) in the solvent A and the solution of phosphoric acid in the solvent B and then performing crystallization.

In some embodiments, a solution of the compound of formula (I) in a solvent A is prepared, wherein the solvent A is selected from the group consisting of acetone, ethyl acetate, and methyl tert-butyl ether.

In some embodiments, a solution of phosphoric acid in a solvent B is prepared, wherein the solvent B is selected from the group consisting of methanol, ethanol, and water.

The present disclosure provides a sulfate of the compound of formula (I), wherein the compound of formula (I) and a sulfuric acid molecule are in an amount-of-substance ratio of 1:1.

The present disclosure provides a crystal form A of the sulfate of the compound of formula (I), wherein the compound of formula (I) and the sulfuric acid molecule are in an amount-of-substance ratio of 1:1, and in an X-ray powder diffraction pattern, the crystal form has characteristic peaks at 2θ angles of diffraction of 6.6, 7.9, 15.1, 20.7, and 22.1.

In some embodiments, the crystal form A of the sulfate of the compound of formula (I) comprises the compound of formula (I) and the sulfuric acid molecule in an amount-of-substance ratio of 1:1, and, in the X-ray powder diffraction pattern, has characteristic peaks at 2θ angles of diffraction of 6.6, 7.9, 13.4, 14.5, 15.1, 19.3, 19.8, 20.7, 22.1, 24.8, 25.4, 25.7, and 27.6.

In some embodiments, the crystal form A of the sulfate of the compound of formula (I) comprises the compound of formula (I) and the sulfuric acid molecule in an amount-of-substance ratio of 1:1, and, in the X-ray powder diffraction pattern, has characteristic peaks at 2θ angles of diffraction of 6.6, 7.9, 11.6, 13.4, 14.5, 15.1, 15.9, 18.1, 19.3, 19.8, 20.7, 22.1, 24.0, 24.8, 25.4, 25.7, 27.2, 27.6, 28.3, and 29.2.

In some embodiments, the crystal form A of the sulfate of the compound of formula (I) comprises the compound of formula (I) and the sulfuric acid molecule in an amount-of-substance ratio of 1:1, and the X-ray powder diffraction pattern at 2θ angles of diffraction is shown in FIG. 8.

In some embodiments, the crystal form A of the sulfate of the compound of formula (I) comprises the compound of formula (I) and the sulfuric acid molecule in an amount-of-substance ratio of 1:1, and belongs to a monoclinic system with axial lengths a=9.7051 (11) Å; b=26.208 (3) Å; c=12.1065 (13) Å; an axial angle β=90°; and a crystal volume V=3079.3 (6) $Å^3$.

The present disclosure provides a method for preparing the sulfate of the compound of formula (I) or the crystal form A of the sulfate of the compound of formula (I), comprising the step of reacting the compound of formula (I) with sulfuric acid.

The present disclosure provides a method for preparing the crystal form A of the sulfate of the compound of formula (I), comprising the following steps:

1) preparing a solution of the compound of formula (I) in a solvent A, wherein the solvent A is selected from the group consisting of a ketone solvent, an ester solvent, a nitrile solvent, and an alcohol solvent;
2) preparing a solution of sulfuric acid in a solvent B, wherein the solvent B is selected from the group consisting of water, a nitrile solvent, and an alcohol solvent; and
3) mixing the solution of the compound of formula (I) in the solvent A and the solution of sulfuric acid in the solvent B and then performing crystallization.

In some embodiments, a solution of the compound of formula (I) in a solvent A is prepared, wherein the solvent A is selected from the group consisting of acetone, ethyl acetate, acetonitrile, methanol, and ethanol.

In some embodiments, a solution of sulfuric acid in a solvent B is prepared, wherein the solvent B is selected from the group consisting of methanol, acetonitrile, ethanol, and water.

The present disclosure provides an amorphous form of a citrate of the compound of formula (I).

The present disclosure provides a method for preparing a citrate of the compound of formula (I), comprising the step of reacting the compound of formula (I) with citric acid to form a salt.

The present disclosure provides an amorphous form of an L-tartrate of the compound of formula (I).

The present disclosure provides a method for preparing an L-tartrate of the compound of formula (I), comprising the step of reacting the compound of formula (I) with L-tartaric acid to form a salt.

The present disclosure provides a method for preparing a hydrochloride of the compound of formula (I), comprising the step of reacting the compound of formula (I) with hydrochloric acid to form a salt.

The present disclosure provides a method for preparing a hydrobromide of the compound of formula (I), comprising the step of reacting the compound of formula (I) with hydrobromic acid to form a salt.

The present disclosure provides a method for preparing a mesylate of the compound of formula (I), comprising the step of reacting the compound of formula (I) with methanesulfonic acid to form a salt.

The present disclosure provides a method for preparing a formate of the compound of formula (I), comprising the step of reacting the compound of formula (I) with formic acid to form a salt.

The present disclosure provides a method for preparing an acetate of the compound of formula (I), comprising the step of reacting the compound of formula (I) with acetic acid to form a salt.

The present disclosure provides a method for preparing a succinate of the compound of formula (I), comprising the step of reacting the compound of formula (I) with succinic acid.

The present disclosure provides a method for preparing a maleate of the compound of formula (I), comprising the step of reacting the compound of formula (I) with maleic acid to form a salt.

The present disclosure provides a method for preparing a malate of the compound of formula (I), comprising the step of reacting the compound of formula (I) with malic acid to form a salt.

The present disclosure provides a method for preparing a p-toluenesulfonate of the compound of formula (I), comprising the step of reacting the compound of formula (I) with p-toluenesulfonic acid to form a salt.

In some embodiments, for the crystal form I of the phosphate of the compound of formula (I) or the crystal form A of the sulfate of the compound of formula (I) provided in the present disclosure, the 2θ angles of the characteristic peaks have a margin of error of 0.2 in the X-ray powder diffraction pattern at 2θ angles of diffraction.

In another aspect, the present disclosure provides a pharmaceutical composition comprising the following ingredients:

1) the phosphate, sulfate, tartrate, citrate, hydrochloride, hydrobromide, mesylate, formate, acetate, succinate, maleate, malate, or p-toluenesulfonate of the compound of formula (I), the crystal form I of the phosphate of the compound of formula (I) or the crystal form A of the sulfate of the compound of formula (I), the amorphous form of the citrate of the compound of formula (I), the amorphous form of the L-tartrate of the compound of formula (I), or a mixture thereof, and
2) optional pharmaceutically acceptable carriers, diluents, or excipients.

In another aspect, the present disclosure provides a method for preparing a pharmaceutical composition comprising the step of mixing 1) the phosphate, sulfate, tartrate, citrate, hydrochloride, hydrobromide, mesylate, formate, acetate, succinate, maleate, malate, or p-toluenesulfonate of the compound of formula (I), the crystal form I of the phosphate of the compound of formula (I) or the crystal form A of the sulfate of the compound of formula (I), the amorphous form of the citrate of the compound of formula (I), the amorphous form of the L-tartrate of the compound of formula (I), or a mixture thereof; and
2) optional pharmaceutically acceptable carriers, diluents, or excipients.

In another aspect, the present disclosure provides use of the phosphate, sulfate, tartrate, citrate, hydrochloride, hydrobromide, mesylate, formate, acetate, succinate, maleate, malate, or p-toluenesulfonate of the compound of formula (I), the crystal form I of the phosphate of the compound of formula (I) or the crystal form A of the sulfate of the compound of formula (I), the amorphous form of the citrate of the compound of formula (I), or the amorphous form of the L-tartrate of the compound of formula (I) described above, or a mixture or a composition thereof in the preparation of a selective estrogen receptor degrader (SERD).

In another aspect, the present disclosure provides use of the phosphate, sulfate, tartrate, citrate, hydrochloride, hydrobromide, mesylate, formate, acetate, succinate, maleate, malate, or p-toluenesulfonate of the compound of formula (I), the crystal form I of the phosphate of the compound of formula (I) or the crystal form A of the sulfate of the compound of formula (I), the amorphous form of the citrate of the compound of formula (I), or the amorphous form of the L-tartrate of the compound of formula (I) described above, or a mixture or a composition thereof in the preparation of a medicament for preventing and/or treating cancer, wherein the cancer is preferably selected from the group consisting of breast cancer, endometrial cancer, uterine cancer, cervical cancer, skin cancer, prostate cancer, ovarian cancer, fallopian tube tumor, hemophilia, and leukemia.

In another aspect, the present disclosure provides use of the phosphate, sulfate, tartrate, citrate, hydrochloride, hydrobromide, mesylate, formate, acetate, succinate, maleate, malate, or p-toluenesulfonate of the compound of formula (I), the crystal form I of the phosphate of the compound of formula (I) or the crystal form A of the sulfate of the compound of formula (I), the amorphous form of the citrate of the compound of formula (I), or the amorphous form of the L-tartrate of the compound of formula (I) described above, or a mixture or a composition thereof in the preparation of a medicament for preventing and/or treating an estrogen receptor-mediated or -dependent disease or condition, wherein preferably, the estrogen receptor-mediated or -dependent disease or condition is selected from the group consisting of cancer, central nervous system deficit, cardiovascular system deficit, blood system deficit, immune and inflammatory disease, susceptible infection, metabolic deficit, neurologic deficit, psychiatric deficit, and reproductive deficit; preferably, the cancer is selected from the group consisting of breast cancer, endometrial cancer, uterine cancer, cervical cancer, skin cancer, prostate cancer, ovarian cancer, fallopian tube tumor, hemophilia, and leukemia; more preferably, the cancer is selected from the group consisting of breast cancer, ovarian cancer, endometrial cancer, prostate cancer, and uterine cancer.

As used herein, "2θ" or "2θ angle" refers to the angle of diffraction, and θ refers to the Bragg angle in ° or degrees; the 2θ of each characteristic peak has a margin of error of ±0.20, and the error may specifically be −0.20, −0.19, −0.18, −0.17, −0.16, −0.15, −0.14, −0.13, −0.12, −0.11, −0.10, −0.09, −0.08, −0.07, −0.06, −0.05, −0.04, −0.03, −0.02, −0.01, 0.00, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, or 0.20.

As used herein, "crystallization" includes, but is not limited to, stirring crystallization, cooling crystallization, solvent out crystallization, and evaporative crystallization.

The "differential scanning calorimetry" or "DSC" described herein refers to measurement of the temperature difference and heat flow difference between a sample and a reference substance during a ramping or thermostatic process to characterize all the physical changes and chemical changes related to the thermal effect, and to obtain the phase change information about the sample.

The drying described herein is generally performed at a temperature of 25° C. to 100° C., preferably 40° C. to 70° C., and may be performed under atmospheric pressure or reduced pressure.

The values in the present disclosure are instrument measurements or calculated values after instrument measurement, and have a certain degree of error. Generally, +10% falls within a reasonable error range. It is certainly necessary to consider the context in which the value is used, for example, for the content of the total impurity, the error range of the value after the measurement shall not exceed ±10%, and may be ±9%, ±8%, ±7%, ±6%, +±5%, ±4%, ±3%, ±2% or ±1%, preferably ±±5%.

The starting materials used in the method for preparing the crystal forms disclosed herein may be any form of the compound of formula (I), including but not limited to: an amorphous form, any crystal form, a hydrate, a solvate, and the like.

As used herein, "crystallization" includes, but is not limited to, stirring crystallization, cooling crystallization, slurry crystallization, and evaporative crystallization.

DETAILED DESCRIPTION

Figure 1:
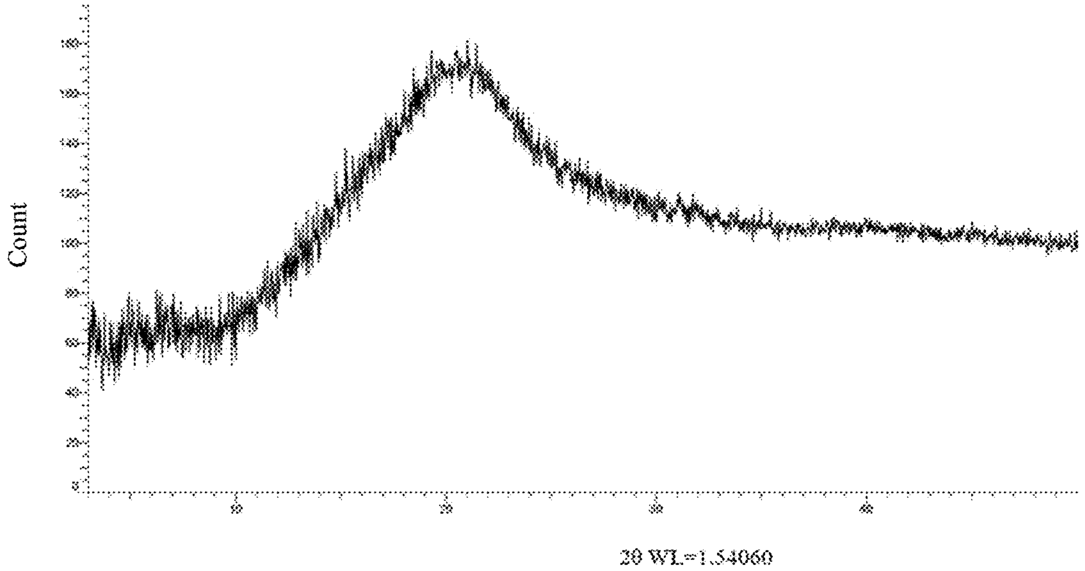
FIG. 1 shows an XRPD pattern of an amorphous form of a compound of formula (I)

The present invention is further illustrated in detail by the following examples and experimental examples. These examples and experimental examples are for illustrative purposes only and are not intended to limit the scope of the present invention.

Test conditions for the instruments used in the experiment:

The structures of compounds were determined by nuclear magnetic resonance (NMR) spectroscopy and/or mass spectrometry (MS). NMR shifts (δ) were given in $10^{-6}$ (ppm). NMR spectra were determined using a Bruker AVANCE-400 nuclear magnetic resonance instrument or Bruker AVANCE NEO 500M, with deuterated dimethyl sulfoxide (DMSO-$d_6$), deuterated chloroform ($CDCl_3$), and deuterated methanol ($CD_3OD$) as determination solvents and tetramethylsilane (TMS) as an internal standard.

MS analyses were performed on an Agilent 1200/1290 DAD-6110/6120 Quadrupole MS liquid chromatography-mass spectrometry system (manufacturer: Agilent; MS model: 6110/6120 Quadrupole MS), Waters ACQuity UPLC-QD/SQD (manufacturer: Waters; MS model: Waters ACQuity Qda Detector/Waters SQ Detector) and THERMO Ultimate 3000-Q Exactive (manufacturer: THERMO; MS model: THERMO Q Exactive).

High-performance liquid chromatography (HPLC) analysis was performed using the Agilent HPLC 1200DAD, Agilent HPLC 1200VWD and Waters HPLC e2695-2489 high-performance liquid chromatographs.

Chiral HPLC analysis was performed on an Agilent 1260 DAD high performance liquid chromatograph.

Preparative HPLC was performed on Waters 2767, Waters 2767-SQ Detecor2, Shimadzu LC-20AP, and Gilson-281 preparative chromatographs.

Preparative chiral chromatography used a Shimadzu LC-20AP preparative chromatograph.

The CombiFlash preparative flash chromatograph used was CombiFlash Rf200 (TELEDYNE ISCO).

XRPD refers to X-ray powder diffraction detection: The measurement was conducted on a BRUKER D8 DISCOVER X-ray diffractometer with a Cu anode (40 kV, 40 mA) and Cu-Kα radiation (λ=1.5418 Å) used. Scan mode: θ/2θ, scan range (2θ range): 3-48°.

DSC refers to differential scanning calorimetry: The measurement was conducted on METTLER TOLEDO DSC 3+ differential scanning calorimeter with a temperature ramp rate of 10° C./min, specific temperature ranges shown in corresponding patterns (25-240° C.), and a nitrogen purge rate of 50 mL/min.

TGA refers to thermogravimetric analysis: The measurement was conducted on METTLER TOLEDO TGA 2 thermogravimetric analyzer with a temperature ramp rate of 10° C./min, specific temperature ranges shown in corresponding patterns (30-350° C.), and a nitrogen purge rate of 20 mL/min.

DVS refers to dynamic vapor sorption: The measurement was conducted on SMS DVS Advantage; at 25° C., the humidity was changed as follows: 50%-95%-0%-95%-50%, in steps of 10% (5% for the last step) (specific humidity ranges are shown in corresponding patterns, and those listed here were used in most cases); the criterion was dm/dt≤0.002%.

Yantai Huanghai HSGF254 or Qingdao GF254 silica gel plates, 0.15-0.2 mm layer thickness, were adopted for thin-layer chromatography (TLC) analysis and 0.4-0.5 mm layer thickness for TLC separation and purification.

Silica gel column chromatography generally used 200- to 300-mesh silica gel (Huanghai, Yantai) as the carrier.

The mean kinase inhibition rates and IC50 values were measured using a NovoStar microplate reader (BMG, Germany).

Known starting materials described herein may be synthesized using or according to methods known in the art, or may be purchased from ABCR GmbH & Co. KG, Acros Organics, Aldrich Chemical Company, Accela ChemBio Inc., Chembee Chemicals, and other companies.

In the examples, reactions can all be performed in an argon atmosphere or a nitrogen atmosphere unless otherwise specified.

The argon atmosphere or nitrogen atmosphere means that the reaction flask is connected to a balloon containing about 1 L of argon or nitrogen.

The hydrogen atmosphere means that the reaction flask is connected to a balloon containing about 1 L of hydrogen.

Pressurized hydrogenation reactions were performed using a Parr 3916EKX hydrogenator and a Qinglan QL-500 hydrogenator, or an HC2-SS hydrogenator.

Hydrogenation reactions generally involved 3 cycles of vacuumization and hydrogen purging.

Microwave reactions were performed on a CEM Discover-S 908860 microwave reactor.

In the examples, a solution was an aqueous solution unless otherwise specified.

In the examples, the reaction temperature was room temperature, i.e., 20° C. to 30° C., unless otherwise specified.

The monitoring of the reaction progress in the examples was conducted by thin-layer chromatography (TLC). The developing solvent for reactions, the eluent system for column chromatography purification and the developing solvent system for thin-layer chromatography included: A: dichloromethane/methanol system, B: n-hexane/ethyl acetate system, and C: petroleum ether/ethyl acetate system. The volume ratio of the solvents was adjusted according to the polarity of the compound, or by adding a small amount of basic or acidic reagents such as triethylamine and acetic acid.

Example 1. Preparation of Compound of Formula 1 (Preparation Method of Example 13 in Application with Priority to 202010680491.4)

2,2-Difluoro-3-((5S,7R)-5-(5-((1-(3-fluoropropyl)azetidin-3-yl)amino)pyridin-2-yl)-7-methyl-7,8-dihydro-[1,3]dioxolo[4,5-g]isoquinolin-6(5H)-yl-2,2-$d_2$)propan-1-ol 1

1

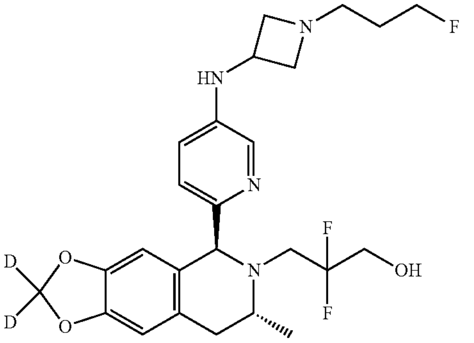

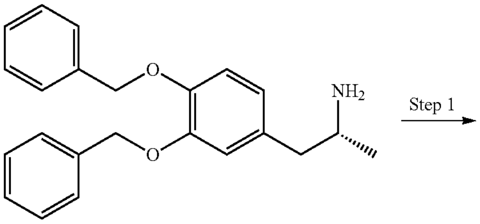

1a

-continued

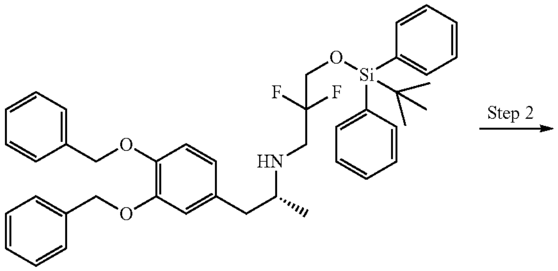

1b

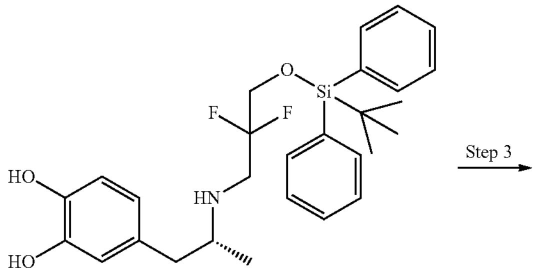

1c

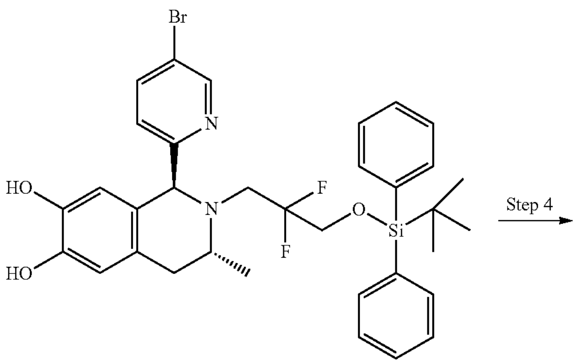

1d

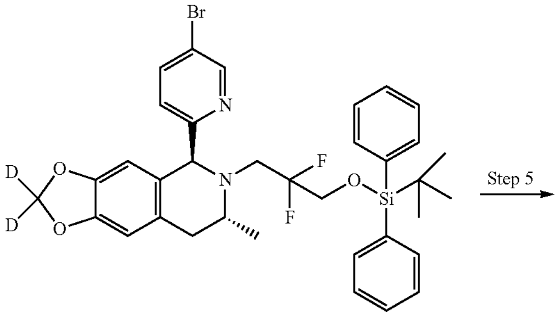

1e

-continued

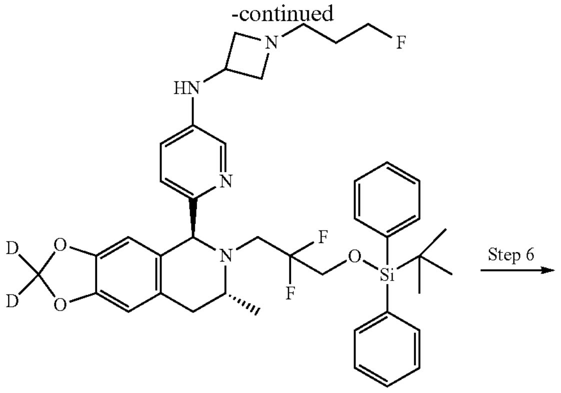

1f

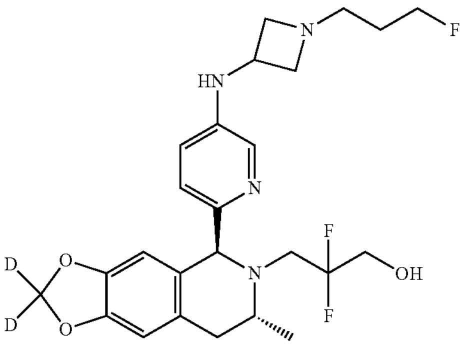

1

Step 1

(R)—N-(1-(3,4-bis(benzyloxy)phenyl)propan-2-yl)-3-((tert-butyldiphenylsilyl)oxy)-2,2-difluoropropan-1-amine 1b Compound 1a (1.0 g, 3.0 mmol) was dissolved in dioxane (20 mL), and diisopropylethylamine (1.2 g, 9.0 mmol) and 3-((tert-butyldiphenylsilyl)oxy)-2,2-difluoropropyltrifluoromethanesulfonate (1.0 g, 2.0 mmol, prepared by using the well-known method in "*Bioorganic & Medicinal Chemistry Letters,* 2018, 28(14), 2528-2532") were added. The reaction mixture was stirred in an oil bath at 80° C. in an argon atmosphere for 20 h. The reaction mixture was cooled and concentrated under reduced pressure. Saturated sodium bicarbonate solution (50 mL) was added, followed by the extraction with ethyl acetate (100 mL×2). The organic phases were combined, dried over anhydrous sodium sulfate, and filtered. The filtrate was concentrated under reduced pressure, and the resulting residue was purified by column chromatography with developing solvent system B to give the title compound 1b (1.7 g, 84% yield). MS m/z (ESI): 680.2 [M+1].

Step 2

(R)-4-(2-((3-((tert-butyldiphenylsilyl)oxy)-2,2-difluoropropyl)amino)propyl)benzene-1,2-diol 1c Compound 1b (1.4 g, 2.0 mmol) was dissolved in methanol (10 mL), and palladium hydroxide on carbon (0.2 g) was added in an argon atmosphere. The reaction mixture was stirred under hydrogen balloon for 3 h, and filtered. The filtrate was concentrated under reduced pressure to give the title compound 1c (0.9 g, 94% yield).

Step 3

(1S,3R)-1-(5-bromopyridin-2-yl)-2-(3-((tert-butyldiphenylsilyl)oxy)-2,2-difluoropropyl)-3-methyl-1,2,3,4-tetrahydroisoquinoline-6,7-diol 1d Compound 1c (0.8 g, 1.6 mmol) was dissolved in toluene (10 mL), and acetic acid (0.2 g, 3.2 mmol) and 5-bromopyridylaldehyde (0.6 g, 3.2 mmol) were added. The reaction mixture was stirred in an oil bath at 80° C. for 16 h, and the reaction was terminated. The reaction mixture was cooled and concentrated under reduced pressure. Water (10 mL) was added, and the reaction mixture was adjusted to about pH 8 by slowly adding saturated sodium bicarbonate solution (20 mL) and extracted with ethyl acetate (10 mL×2). The organic phases were combined, dried over anhydrous sodium sulfate, and filtered. The filtrate was concentrated under reduced pressure, and the resulting residue was purified by column chromatography with developing solvent system B to give the title compound 1d (256 mg, 75% yield).

MS m/z (ESI): 667.1 [M+1].

Step 4

(5S,7R)-5-(5-bromopyridin-2-yl)-6-(3-((tert-butyldiphenylsilyl)oxy)-2,2-difluoropropyl)-7-methyl-5,6,7,8-tetrahydro-[1,3]dioxolo[4,5-g]isoquinoline-2,2-$d_2$ 1e Compound 1d (350 mg, 0.5 mmol) was dissolved in N,N-dimethylformamide (10 mL), and dibromodideuteromethane (277 mg, 1.6 mmol) and cesium carbonate (512 mg, 1.6 mmol) were added. The reaction mixture was stirred in an oil bath at 70° C. for 16 h, and the reaction was terminated. The reaction mixture was cooled and concentrated under reduced pressure. Water (10 mL) was added, followed by the extraction with ethyl acetate (10 mL×2). The organic phases were combined, dried over anhydrous sodium sulfate, and filtered. The filtrate was concentrated under reduced pressure, and the resulting residue was purified by column chromatography with developing solvent system B to give the title compound 1e (170 mg, 48% yield).

MS m/z (ESI): 681.1 [M+1].

Step 5

6-((5S,7R)-6-(3-((tert-butyldiphenylsilyl)oxy)-2,2-difluoropropyl)-7-methyl-5,6,7,8-tetrahydro-[1,3]dioxolo[4,5-g]isoquinolin-5-yl-2,2-$d_2$)—N-(1-(3-fluoropropyl)azetidin-3-yl)pyridin-3-amine 1f Compound 1e (170 mg, 0.25 mmol) was dissolved in dioxane (10 mL), and the compound 1-(3-fluoropropyl)azetidin-3-amine (prepared as disclosed in "Example 1 on page 50 of the specification of Patent Application WO2019228443", 44 mg, 0.3 mmol), 2,2'-bis-(diphenylphosphino)-1,1'-binaphthyl (12 mg, 0.02 mmol), tris(dibenzylideneacetone)dipalladium(0) (20 mg, 0.02 mmol), and sodium tert-butoxide (29 mg, 0.3 mmol) were added in an argon atmosphere. The reaction mixture was stirred in an oil bath at 80° C. for 16 h, and the reaction was terminated. The reaction mixture was cooled and concentrated. Saturated sodium bicarbonate solution (10 mL) was added, followed by the extraction with ethyl acetate (10 mL×2). The organic phases were combined, dried over anhydrous sodium sulfate, and filtered. The filtrate was concentrated under reduced pressure, and the resulting residue was purified by column chromatography with developing solvent system B to give the title compound 1f (47 mg, 51% yield).

Step 6

2,2-Difluoro-3-((5S,7R)-5-(5-((1-(3-fluoropropyl)azetidin-3-yl)amino)pyridin-2-yl)-7-methyl-7,8-dihydro-[1,3]dioxolo[4,5-g]isoquinolin-6(5H)-yl-2,2-$d_2$)propan-1-ol 1

Compound 1f (103 mg, 0.14 mmol) was dissolved in dichloromethane (5 mL), and a 1 M solution of n-tetrabutylammonium fluoride in tetrahydrofuran (1 mL) was added dropwise in an ice bath. After addition, the reaction mixture was stirred at room temperature for 1.5 h and concentrated under reduced pressure. Saturated sodium bicarbonate solution (5 mL) was added, followed by the extraction with ethyl acetate (5 mL×3). The organic phases were combined, washed with saturated sodium chloride solution (5 mL), dried over anhydrous sodium sulfate, and filtered. The filtrate was concentrated under reduced pressure, and the resulting residue was purified by column chromatography with developing solvent system B to give the title compound 1 (11 mg, 42% yield).

MS m/z (ESI): 495.2 [M+1].

$^1H$ NMR (400 MHz, $CD_3OD$) 7.80 (d, 1H), 7.04 (d, 1H), 6.94 (dd, 1H), 6.61 (s, 1H), 6.19 (s, 1H), 4.64 (br, 2H), 4.54-4.52 (m, 1H), 4.45-4.42 (m, 1H), 4.15-4.10 (m, 1H), 3.85-3.83 (m, 2H), 3.76-3.68 (m, 1H), 3.64-3.56 (m, 1H), 3.14-2.97 (m, 4H), 2.78-2.68 (m, 3H), 2.59-2.52 (m, 1H), 1.84-1.74 (m, 2H), 1.05 (d, 3H).

The product was identified by X-ray powder diffraction as amorphous. The XRPD pattern is shown in FIG. 1.

Biological Evaluation

The present disclosure is further described and explained below with reference to test examples, but these examples are not intended to limit the scope of the present disclosure.

Test Example 1. Inhibition of Binding of E to ER by Compound Disclosed Herein The compound of the present disclosure can inhibit the binding of E (estrogen) to ER (estrogen receptor), thereby blocking the binding of the complex of E and ER to ERE (estrogen response element), and consequently the expression of downstream luciferase proteins. The inhibitory effect of the compound of the present disclosure on the binding of E to ER was tested by using the following method.

1. Objective

This experiment is intended to test the inhibitory effect of the compound on the binding of E to ER, and to evaluate the in vitro activity of the compound according to the $IC_{50}$ value.

2. Method

An ERE was cloned upstream of the luciferase gene, and MCF-7/ERE-luciferase monoclonal cells were selected by transfection of MCF-7 (TCHu74, National Collection of Authenticated Cell Cultures). The MCF-7/ERE-luciferase cells were seeded into a 96-well plate with an MEM (hyclone, SH30024.01B) medium containing 10% charcoal stripped FBS (Moregate, FBSF), 1% sodium pyruvate (sigma, S8636), 1% non-essential amino acids (sigma, M7145) and 500 μg/mL G418 at a density of 30,000 cells/well and cultured at 37° C. with 5% $CO_2$. 20 mM stock solutions of the drugs were prepared, serially diluted 10-fold with 100% DMSO, and then diluted 20-fold with the medium. After the cells were cultured for 24 h, the medium was removed. 0.1 nM estradiol (sigma, E2758) and 10 μL of a medium-diluted drug were added to each well, and DMSO was added to the control group. The mixtures were well mixed by gentle shaking. The cells were cultured in an incubator at 37° C. with 5% $CO_2$ for 24 h, and then the cell culture liquid was removed, followed by the addition of 50 μL of a luciferase substrate (Promega, E6110) to each well. The plate was let stand at room temperature in the dark for 10-15 min, and the chemiluminescence signal value was determined.

3. Test Results

The inhibitory effect of the compound of the present disclosure on the binding of E to ER was determined through the above experiment. The chemiluminescence signal value was analyzed against the compound concentration (in log form) using Graphpad Prism, and the $IC_{50}$ value of the compound was obtained. The result is shown in Table 1.

TABLE 1

Inhibitory effect of the compound disclosed herein on the binding of E to ER

| Compound No. | $IC_{50}$ (nM) |
|---|---|
| 1 | 0.69 |

Conclusion: The compound claimed by the present disclosure had a significant inhibitory effect on the binding of E to ER.

Test Example 2. Inhibitory Effect of Compound Disclosed Herein on Proliferation of MCF-7 Cells 1. Objective This experiment was intended to test the inhibitory effect of the compound disclosed herein on the proliferation of MCF-7 cells by using the ATP method, and to evaluate the in vitro activity of the compound according to the $IC_{50}$ value.

2. Method

MCF-7 cells (TCHu74, National Collection of Authenticated Cell Cultures) were seeded into a 96-well plate with an MEM (hyclone, SH30024.01B) medium containing 10% FBS (Gibco, 10099-141), 1% sodium pyruvate (sigma, S8636) and 1% non-essential amino acid (sigma, M7145) at a density of 4,000 cells/well and cultured at 37° C. with 5% $CO_2$. 20 mM stock solution of the compound was prepared, serially diluted with 100% DMSO to a final concentration of 1000×, and then diluted 20-fold with a medium containing 2% FBS. After the cells were cultured for 24 h, the medium was removed. 90 μL of the medium containing 2% FBS and 10 μL of a drug were added to each well, and 10 μL of DMSO was added to the control group. The mixtures were well mixed by gentle shaking. The blank group contained only 100 μL of the medium containing 2% FBS. The cells were cultured in an incubator at 37° C. with 5% $CO_2$ for 72 h, and then 50 μL of mixed Cell Titer-Glo (Promega, G7571) was added to each well. The mixtures were well mixed by shaking and let stand at room temperature for 10 min, and the chemiluminescence signal value was determined.

3. Data Analysis

The chemiluminescence signal value was plotted against the compound concentration (in log form) using Graphpad Prism, and the $IC_{50}$ value of the compound was obtained. The result is shown in Table 2.

TABLE 2

| Inhibitory effect of the compound disclosed herein on proliferation of MCF-7 cells | |
|---|---|
| Compound No. | $IC_{50}$ (nM) |
| 1 | 0.29 |

Test Example 3. Biological Evaluation of Inhibition of Proliferation of ERα Mutant-Expressing MCF7 Cells by Compound Disclosed Herein 1. Objective The objective of this experiment was to determine the inhibitory activity of the compound of the present disclosure on the proliferation of ERα mutant-expressing MCF7 cells.

2. Method

Site-Directed Mutagenesis and Cell Line Construction

The mutant estrogen receptor α (ERα) Y537S of human ERα protein was obtained by site-directed mutagenesis in a two-primer PCR manner using the cDNA of wild-type ESR1 gene (Accession No. NM000125) as a template. The sequences of the primers used in the mutation are as follows (the underlined nucleotides are the sites of mutation): Y537S: F-AAG AAC GTG GTG CCC CTC TCT GAC CTG CTG CTG GAG ATG (SEQ ID NO: 1); R-CAT CTC CAG CAG CAG GTC AGA GAG GGG CAC CAC GTT CTT (SEQ ID NO: 2). The cDNA of the mutant ESR1 was cloned into the lentiviral vector of interest pCDH-CMV-MCS-EF1-Puro. The lentiviral plasmid bearing the mutant ESR1 gene sequence and the lentiviral packaging plasmid were then transfected into HEK-293T cells (ATCC, CRL-3216) by using Lipofectamine 3000 Transfection Reagent (ThermoFisher Scientific, Cat #L3000075). Forty-eight hours after transfection, the virus-bearing medium supernatant was filtered and ultracentrifuged to obtain a virus precipitate, which was then resuspended in an appropriate amount of medium. The suspension was added to MCF7 cells (ATCC, HTB-22), followed by the addition of polybrene at a final concentration of 8 μg/mL. The mixture was incubated overnight. Two days after transfection, 1 μg/mL puromycin was added to the cell culture liquid for resistance screening. About two weeks later, an MCF7 cell line capable of stably expressing the ERαY537S mutant was obtained.

Cell Proliferation Inhibition Assay

The ERα mutant-expressing MCF7 cells were cultured in an MEM (GE Healthcare, SH30024.01) complete medium containing 10% fetal bovine serum. On the first day of the experiment, the cells were seeded into a 96-well plate with a complete medium at a density of 3,000 cells/well to form 100 μL of cell suspension per well. The plate was incubated overnight in a cell incubator at 37° C. with 5% $CO_2$. The next day, the medium was removed, and 135 μL of an MEM incomplete medium containing 2% fetal bovine serum, and 15 μL of a test compound prepared at different concentrations with the incomplete medium were added to each well. The final concentration of the compound was 9 concentration points obtained by 4-fold serial dilution from 100 nM. A blank control containing 0.5% DMSO was set. The plate was incubated in a cell incubator at 37° C. with 5% $CO_2$ for 144 h. On day 8, the 96-well cell culture plate was taken out. 150 μL of CellTiter-Glo® Luminescent Cell Viability Assay (Promega, G7573) was added to each well. The plate was let stand at room temperature for 10 min, and the luminescence signal value was read using a multilabel microplate reader (PerkinElmer, VICTOR 3). The $IC_{50}$ value for the inhibitory activity of the compound was calculated according to the compound concentration and the luminescence signal value and is shown in Table 3.

3. Test Results

TABLE 3

| $IC_{50}$ value for the inhibitory effect of the compound disclosed herein on the proliferation of ERα mutant-expressing MCF7 cells | |
|---|---|
| Compound No. | $IC_{50}$ (nM) |
| 1 | 1.36 |

Conclusion: The compound claimed by the present disclosure showed a significant inhibitory effect on the proliferation of ERα mutant-expressing MCF7 cells.

Test Example 4. Degradation of ERα by Compound Disclosed Herein

1. Objective

This experiment was intended to test the degradation of ERα by the compound disclosed herein. This method was used to determine the degradation of ERα by the compound disclosed herein.

2. Method

ERα-positive breast cancer cell line MCF-7 cells were cultured in a DMEM/F12 medium (HyClone, SH30023.01) containing 10% fetal bovine serum (Corning, 35-010-CV). On the first day of the experiment, after being digested, the cells were washed once with a phenol red-free DMEM/F12 medium (ThermoFisher, 11039-021) containing 5% charcoal stripped fetal bovine serum (BIOSUN, BS-0004-500), then resuspended, and counted, and the cell density was adjusted to $1.79\times10^5$ cells/mL. 280 μL of the cell suspension was added to each well of a 48-well plate (Corning, 3548), and the cells were cultured overnight in an incubator at 37° C. with 5% $CO_2$. The next day, the compound was serially diluted with DMSO and further diluted with a phenol red-free DMEM/F12 medium containing 5% charcoal stripped fetal bovine serum. 20 L of a diluted compound was added to each well of the 48-well plate at final concentrations of 3000, 300, 30, 3, 0.3, 0.03 and 0.003 nM. The 48-well plate was placed in the incubator for 16 to 18 h. A 96-well plate was coated with the capture antibody from the human ERα/NR3A1 total protein assay kit (R&D, DYC5715-5). 1 μg/mL capture antibody was prepared in PBS, and 100 L of the antibody was added to each well of the 96-well plate (Corning, 3590). The plate was placed in an incubator at 26° C. overnight. On day 3, the antibody-coated 96-well plate was washed once with PBS, and 200 μL of PBS containing 1% BSA was added to each well. The plate was incubated in an incubator at 37° C. for 1.5 h to be blocked. The cell culture medium supernatant was discarded. The cells were washed once with PBS, and a cell lysis buffer was added at 60 μL/well. The cell lysis buffer was PBS containing 6 M urea, 1 mM EDTA, 0.5% TritonX-100, 1 mM PMSF and a protease inhibitor (Roche, 04693159001). The cells were lysed on ice for 15 min, and 300 μL of PBS containing 1 mM EDTA and 0.5% TritonX-100 was added to each well to dilute the urea to 1 M. The blocking solution in the blocked 96-well plate was discarded, and the diluted cell lysis buffer was added at 100 μL/well. The plate was incubated in a 37° C. incubator for 2 h and washed five times with PBS. A biotinylated assay antibody was diluted to 0.4 μg/mL with PBS containing 1% BSA, and then 100 μL of the assay antibody was added to each well. The plate was incubated in an incubator at 37° C. for 1 h. The plate was then washed five more times, and 100 μL of avidin-HRP diluted 200-fold with PBS containing 1% BSA was added to each well. The plate was incubated at 37° C. for 30 min. Then the plate was washed five more times, and the TMB substrate was added at 100 μL/well. The plate was incubated at room temperature until the color blue appeared, and a stop solution was added at 100 μL/well. OD450 signal readings were taken on a PHERAstar multi-mode microplate reader. The $IC_{50}$ value for the inhibitory activity of the compound was calculated using Graphpad Prism software. The maximum degradation rate of the compound is the ratio of the level of ERα remaining in the cells after the cells were treated with 3000 nM compound to the level of ERα remaining in cells after the cells were treated with 3000 nM fulvestrant.

3. Test Results

The $EC_{50}$ value determined for the compound disclosed herein in the degradation of ERα is shown in Table 4.

TABLE 4

Degradation of ERα by the compound disclosed herein

| Example No. | $EC_{50}$ (nM) | Emax degradation (%) |
|---|---|---|
| Fulvestrant | 0.06 | 100 |
| 1 | 0.38 | 107 |

Conclusion: The compound claimed by the present disclosure showed a significant degrading effect on ERα.

Test Example 5. Inhibition of Enzymatic Activity of Site of Metabolism of Midazolam in Human Liver Microsome CYP3A4 by Compound Disclosed Herein The inhibition of the enzymatic activity of the site of metabolism of midazolam in human liver microsome CYP3A4 by the compound disclosed herein was determined by using the following method.

I. Experimental Materials and Instruments

1. Phosphate buffer (20×PBS, purchased from Sangon);
2. NADPH (ACROS, A2646-71-1);
3. Human liver microsome (Corning Gentest, Cat No. 452161, Lot No. 9050002, Donor, 36);
4. ABI QTrap 4000 LC-MS System (AB Sciex);
5. ZORBAX Extend-C18, 3×50 mm, 3.5 m (Agilent, USA);
6. CYP probe substrate (midazolam, TRC, M343000/3 μM) and positive control inhibitor (ketoconazole, SIGMA, Cat No. K1003-100MG).

II. Experimental Procedures

A 100 mM PBS buffer was prepared. A 0.25 mg/mL microsome solution, a 7.5 mM $MgCl_2$ and a 5 mM NADPH solution were prepared using the buffer. A 30 mM stock solution was diluted with DMSO to obtain 30 mM, 10 mM, 3 mM, 1 mM, 0.3 mM, 0.03 mM, 0.003 mM and 0 mM serial solutions I, which were further diluted 200-fold with phosphate buffer (PBS) to obtain serial test solutions II (150, 50, 15, 5, 1.5, 0.15, 0.015 and 0 μM). A midazolam working solution was diluted with PBS to 15 μM. 40 μL of a 0.25 mg/mL microsome solution prepared in 7.5 mM $MgCl_2$ and 20 μL of each of the M midazolam working solution and the compound working solutions (150, 50, 15, 5, 1.5, 0.15, 0.015 and 0 μM) were measured out and well mixed. Ketoconazole at the same concentration was used in place of the compound as a positive control group. A 5 mM NADPH solution was simultaneously pre-incubated for 5 min at 37° C. After 5 min, 20 μL of NADPH was added to each well to start the reaction, and the system was incubated for 30 min. Duplicate samples were set for all of the incubated samples. After 30 min, 250 μL of internal standard-containing acetonitrile was added to all the samples. The mixtures were well mixed, shaken at 800 rpm for 10 min, and then centrifuged at 3700 rpm for 10 min. 100 μL of the supernatant and 80 μL of ultrapure water were well mixed and subjected to LC-MS/MS analysis.

The $IC_{50}$ value of the drug for the site of metabolism of midazolam in CYP3A4 was calculated by Graphpad Prism and is shown in Table 5.

TABLE 5

$IC_{50}$ value of the compound disclosed herein for the site of metabolism of midazolam in human liver microsome CYP3A4

| Compound No. | $IC_{50}$ (μM) |
|---|---|
| 1 | 15.38 |

Conclusion: The compound claimed by the present disclosure had a weak inhibitory effect on the site of metabolism of midazolam in human liver microsome CYP3A4, showing better safety, suggesting that metabolic drug interaction based on the site of metabolism of midazolam in CYP3A4 does not occur.

Test Example 6. Inhibition of Enzymatic Activity of Site of Metabolism of Testosterone in Human Liver Microsome CYP3A4 by Compound Disclosed Herein The inhibition of the enzymatic activity of the site of metabolism of testosterone in human liver microsome CYP3A4 by the compound disclosed herein was determined by using the following method.

I. Experimental Materials and Instruments

1. Phosphate buffer (20×PBS, purchased from Sangon);
2. NADPH (ACROS, A2646-71-1);
3. Human liver microsome (Corning Gentest, Cat No. 452161, Lot No. 905002, Donor36);
4. ABI QTrap 4000 LC-MS System (AB Sciex);
5. ZORBAX Extend-C18, 3×50 mm, 3.5 m (Agilent, USA);
6. CYP probe substrate (testosterone, Vocko, CAS No. [58-22-0]/75 μM) and positive control inhibitor (ketoconazole, SIGMA, Cat No. K1003-100MG).

II. Experimental Procedures

A 100 mM PBS buffer was prepared. A 100 mM PBS buffer was prepared. A 0.25 mg/mL microsome solution, a 7.5 mM $MgCl_2$ and a 5 mM NADPH solution were prepared using the buffer. A30 mM stock solution was diluted with DMSO to obtain 30 mM, 10 mM, 3 mM, 1 mM, 0.3 mM, 0.03 mM, 0.003 mM and 0 mM serial solutions I, which were further diluted 200-fold with phosphate buffer (PBS) to obtain serial test solutions II (150, 50, 15, 5, 1.5, 0.15, 0.015 and 0 μM). A testosterone working solution was diluted with PBS to 375 μM. 40 μL of a 0.25 mg/mL microsome solution prepared in 7.5 mM $MgCl_2$ and 20 μL of each of the 375 μM testosterone working solution and the compound working solutions (150, 50, 15, 5, 1.5, 0.15, 0.015 and 0 μM) were measured out and well mixed. Ketoconazole at the same concentration was used in place of the compound as a positive control group. A 5 mM NADPH solution was simultaneously pre-incubated for 5 min at 37° C. After 5 min, 20 μL of NADPH was added to each well to start the reaction, and the system was incubated for 30 min. After 30 min, 250 μL of internal standard-containing acetonitrile was added to all the samples. The mixtures were well mixed, shaken at 800 rpm for 10 min, and then centrifuged at 3700 rpm for 10 min. 100 μL of the supernatant and 80 μL of ultrapure water were well mixed and subjected to LC-MS/MS analysis.

The $IC_{50}$ value of the drug for the site of metabolism of testosterone in CYP3A4 was calculated by Graphpad Prism and is shown in Table 6.

TABLE 6

$IC_{50}$ value of the compound disclosed herein for the site of metabolism of testosterone in human liver microsome CYP3A4

| Compound No. | $IC_{50}$ (μM) |
|---|---|
| 1 | >30 |

Conclusion: The compound claimed by the present disclosure had a weak inhibitory effect on the site of metabolism of testosterone in human liver microsome CYP3A4, showing better safety.

Test Example 7. Time-Dependent Inhibition of Enzymatic Activity of Site of Metabolism of Midazolam in Human Liver Microsome CYP3A4 by Compound Disclosed Herein The time-dependent inhibition of the CYP enzymatic activity of the site of metabolism of midazolam in human liver microsome CYP3A4 by the compound disclosed herein was determined by using the following method.

I. Experimental Materials and Instruments

1. Phosphate buffer (20×PBS, purchased from Sangon);
2. NADPH (ACROS, A2646-71-1);
3. Human liver microsome (Corning Gentest, Cat No. 452161, Lot No. 9050002, Donor, 36);
4. ABI QTrap 4000 LC-MS System (AB Sciex);
5. ZORBAX Extend-C18, 3×50 mm, 3.5 m (Agilent, USA);
6. CYP probe substrate (midazolam, TRC, M343000/3 μM) and positive control inhibitor (verapamil, Adamas Reagent Co., Ltd, Cat No. 25904A).

II. Experimental Procedures

A 100 mM PBS buffer was prepared. A 0.25 mg/mL microsome solution, a 7.5 mM $MgCl_2$ and a 5 mM NADPH solution were prepared using the buffer. A 30 mM stock solution was diluted with DMSO to obtain 30 mM, 10 mM, 3 mM, 1 mM, 0.3 mM, 0.1 mM, 0.03 mM and 0 mM serial solutions I, which were further diluted 200-fold with phosphate buffer (PBS) to obtain serial test solutions II (150, 50, 15, 5, 1.5, 0.5, 0.15 and 0 μM). A midazolam working solution was diluted with PBS to 15 μM.

The serial test solutions prepared above were well mixed by shaking and aliquoted in 20 μL portions into corresponding reaction plates (+NADPH, T0 and -NADPH groups were set). Three parallel tests were set. 40 μL of the liver microsome working solution was added to each 96-well plate. 20 μL of a corresponding substrate solution was added to the TO plate. 20 μL of NADPH was added to the TO plate and +NADPH group. A timer was started, and the plates were incubated in a water bath at 37° C. After 30 min of incubation, the TO plate was taken out, and the reaction was terminated with 250 μL of an internal standard-containing ACN solution. The +NADPH group was supplemented with 20 μL of the corresponding substrate solution, and the −NADPH group was supplemented with 20 μL of the corresponding substrate solution and 20 μL of NADPH. A timer was started, and the plates were incubated in a water bath at 37° C. After 30 min of incubation, the plates were taken out, and the reactions were terminated with 250 μL of an internal standard-containing ACN solution. Then the plates were shaken on a shaker at 800 rpm for 10 min and centrifuged on a centrifuge at 4000 rpm for 15 min. 100 μL of the supernatant and 80 μL of ultrapure water were well mixed and subjected to LC-MS/MS analysis.

The $IC_{50}$ value of the drug for the site of metabolism of midazolam in CYP3A4 was calculated by Graphpad Prism and is shown in Table 7.

TABLE 7

$IC_{50}$ value and $IC_{50}$ shift of the compound disclosed herein for the site of metabolism of midazolam in human liver microsome CYP3A4

| Compound No. | (+)NADPH $IC_{50}$ (μM) | (−)NADPH $IC_{50}$ (μM) | $IC_{50}$ Shift |
|---|---|---|---|
| 1 | 13.11 | 19.59 | 0.7 |

Conclusion: The compound claimed by the present disclosure had a weak inhibitory effect on the site of metabolism of midazolam in human liver microsome CYP3A4, showing better safety, suggesting that metabolic drug interaction based on the site of metabolism of midazolam in CYP3A4 does not occur.

Test Example 8. Time-Dependent Inhibition of Enzymatic Activity of Site of Metabolism of Testosterone in Human Liver Microsome CYP3A4 by Compound Disclosed Herein The time-dependent inhibition of the enzymatic activity of the site of metabolism of testosterone in human liver microsome CYP3A4 by the compound disclosed herein was determined by using the following method.

I. Experimental Materials and Instruments

1. Phosphate buffer (20×PBS, purchased from Sangon);
2. NADPH (ACROS, A2646-71-1);
3. Human liver microsome (Corning Gentest, Cat No. 452161, Lot No. 905002, Donor36);
4. ABI QTrap 4000 LC-MS System (AB Sciex);
5. ZORBAX Extend-C18, 3×50 mm, 3.5 m (Agilent, USA);
6. CYP probe substrate (testosterone, Vocko, CAS No. [58-22-0]/75 μM) and positive control inhibitor (verapamil, Adamas Reagent Co., Ltd, Cat No. 25904A).

II. Experimental Procedures

A 100 mM PBS buffer was prepared. A 0.25 mg/mL microsome solution, a 7.5 mM $MgCl_2$ and a 5 mM NADPH solution were prepared using the buffer. A 30 mM stock solution was diluted with DMSO to obtain 30 mM, 10 mM, 3 mM, 1 mM, 0.3 mM, 0.1 mM, 0.03 mM and 0 mM serial solutions I, which were further diluted 200-fold with phosphate buffer (PBS) to obtain serial test solutions II (150, 50, 15, 5, 1.5, 0.5, 0.15 and 0 μM). A midazolam working solution was diluted with PBS to 15 μM.

The serial test solutions prepared above were well mixed by shaking and aliquoted in 20 μL portions into corresponding reaction plates (+NADPH, TO and -NADPH groups were set). Three parallel tests were set. 40 μL of the liver microsome working solution was added to each 96-well plate. 20 μL of a corresponding substrate solution was added to the TO plate. 20 μL of NADPH was added to the TO plate and +NADPH group. A timer was started, and the plates were incubated in a water bath at 37° C. After 30 min of incubation, the TO plate was taken out, and the reaction was terminated with 250 μL of an internal standard-containing ACN solution. The +NADPH group was supplemented with 20 μL of the corresponding substrate solution, and the −NADPH group was supplemented with 20 μL of the corresponding substrate solution and 20 μL of NADPH. A timer was started, and the plates were incubated in a water bath at 37° C. After 30 min of incubation, the plates were taken out, and the reactions were terminated with 250 μL of an internal standard-containing ACN solution. Then the plates were shaken on a shaker at 800 rpm for 10 min and centrifuged on a centrifuge at 4000 rpm for 15 min. 100 μL of the supernatant and 80 μL of ultrapure water were well mixed and subjected to LC-MS/MS analysis.

The $IC_{50}$ value of the drug for the site of metabolism of testosterone in CYP3A4 was calculated by Graphpad Prism and is shown in Table 8.

TABLE 8

$IC_{50}$ value and $IC_{50}$ shift of the compound disclosed herein for the site of metabolism of testosterone in human liver microsome CYP3A4

| Compound No. | (+)NADPH $IC_{50}$ (μM) | (−)NADPH $IC_{50}$ (μM) | $IC_{50}$ Shift |
|---|---|---|---|
| 1 | >30 | >30 | No TDI |

Conclusion: The compound claimed by the present disclosure had a weak inhibitory effect on the site of metabolism of testosterone in human liver microsome CYP3A4, showing better safety, suggesting that metabolic drug interaction based on CYP3A4 does not occur.

Test Example 9

1. Objective

The blocking of hERG potassium currents by the compound disclosed herein was tested in a stable cell strain transfected with hERG potassium channels using automated patch clamp.

2. Method 2.1. Materials and Instruments 2.1.1. Materials:

| Reagent | Supplier | Cat. No. |
|---|---|---|
| FBS | GIBCO | 10099 |
| Sodium pyruvate solution | sigma | S8636-100ML |
| MEM non-essential amino acid solution (100×) | sigma | M7145-100ML |
| G418 sulfate | Enzo | ALX-380-013-G005 |
| MEM | Hyclone | SH30024.01B |
| hERG cDNA | Synthesized by GENEWIZ | Gene sequence NM_000238.4- |

2.1.2. Instruments:

| Instrument | Supplier | Model |
|---|---|---|
| Patchliner 4 channel | nanion | 2-03-03100-002 |
| Patchliner cleaning station | nanion | 2-02-03201-005 |
| Patchliner cell bank | nanion | 2-02-03105-000 |
| Elektrodenchloridierer Patchliner | nanion | 3-02-03533-000 |
| HEAK EPC10 patch clamp amplifier | nanion | 1-01-10012-000 |
| Osmometer | Gonoter | Gonoter 030 |
| pH meter | Mettle Toledo | FE20 |

2.2. Procedures of Automated Patch Clamp

Stably-expressed HEK293-hERG cell strains were subcultured at a density of 1:4 in an MEM/EBSS medium (10% FBS, 400 μg/mL G418, 1% MEM non-essential amino acid solution (100×), and 1% sodium pyruvate solution) and subjected to an automated patch clamp experiment within 48-72 h after the start of the culture. On the day of the experiment, the cells were digested with 0.25% pancreatin, then centrifuged, collected, and resuspended in an extracellular fluid (140 mM NaCl, 4 mM KCl, 1 mM $MgCl_2$, 2 mM $CaCl_2$, 5 mM D-glucose monohydrate, 10 mM Hepes, pH 7.4, 298 mOsm) to form a cell suspension. The cell suspension was placed on the cell bank of the Patchliner instrument that transferred the cells to the chip (NPC-16) using a negative pressure controller. The negative pressure drew individual cells to the wells of the chip. When a whole-cell model was formed, the instrument generated hERG currents according to the setting of hERG current voltage program, and automatically perfused the compound solutions from low concentrations to high concentrations. Data were recorded and analyzed using the HEAK Patchmaster, HEAK EPC10 patch clamp amplifier (Nanion), Pathliner software and Pathcontrol HTsoftware, and the current of the compound at each concentration and the current of the blank control were analyzed.

2.3. Results

The blocking effect of the compound of the present disclosure on hERG potassium currents was determined by the above test. The $IC_{50}$ value obtained is shown in Table 9.

TABLE 9

$IC_{50}$ of the compound disclosed herein for the blocking of hERG potassium currents

| Compound No. | $IC_{50}$ (μM) |
|---|---|
| 1 | >30 |

Note: $IC_{50}$≥30 μM indicates no inhibitory activity; 30>$IC_{50}$≥10 μM indicates weak inhibitory activity; 10>$IC_{50}$≥1 μM indicates moderate inhibitory activity; $IC_{50}$<1 μM indicates strong inhibitory activity.

Conclusion: The compound claimed by the present disclosure had no inhibitory activity against hERG, showing better safety.

Example 2. Preparation of Crystal Form I of Phosphate of Compound of Formula (I)

Figure 2:
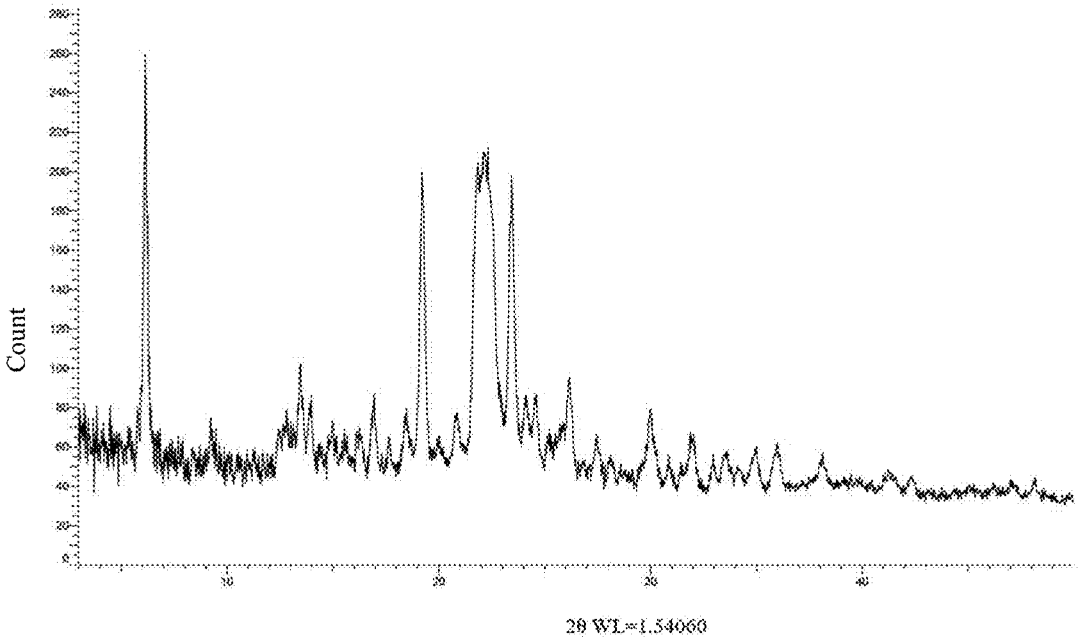
FIG. 2 shows an XRPD pattern of a crystal form I of a phosphate of the compound of formula (I)
Figure 3:
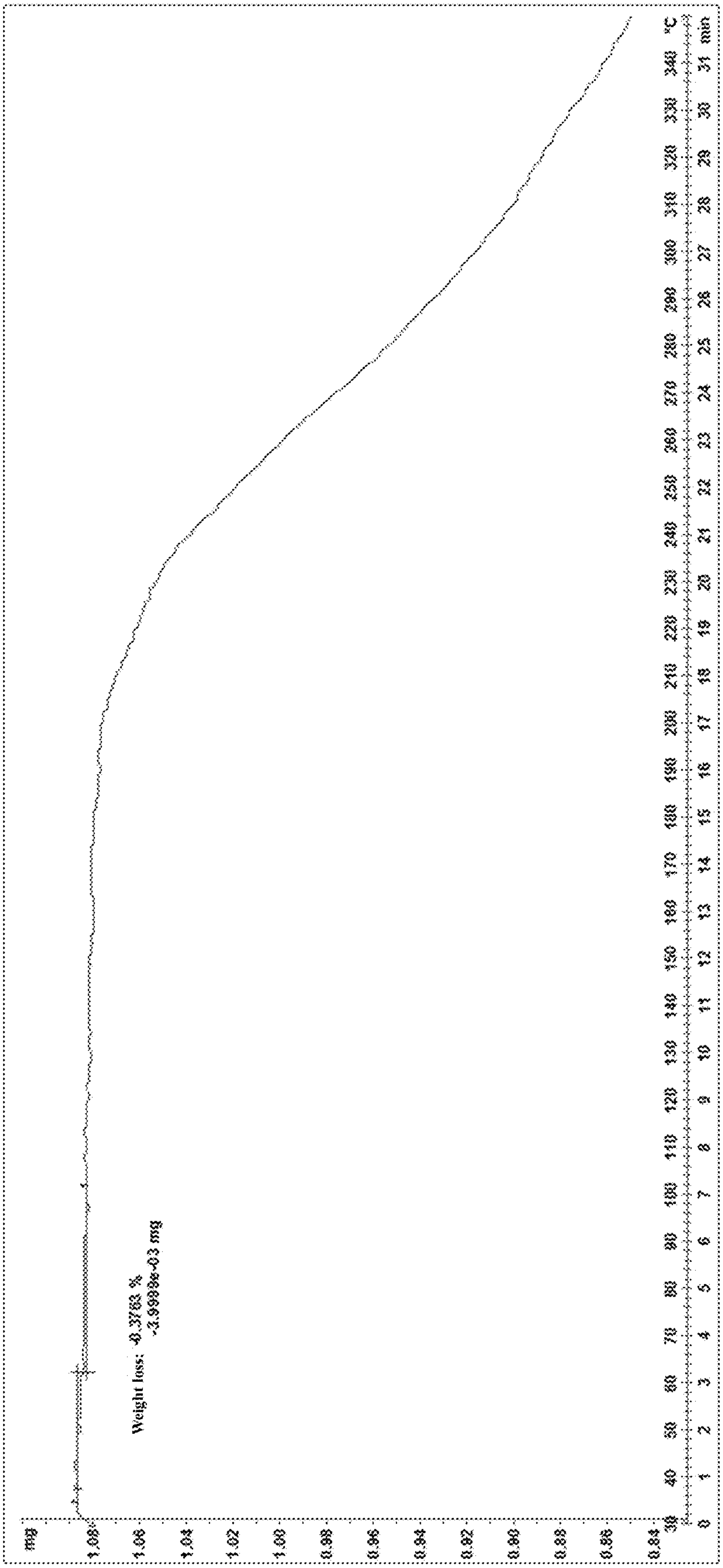
FIG. 3 shows a TGA pattern of the crystal form I of the phosphate of the compound of formula (I)
Figure 4:
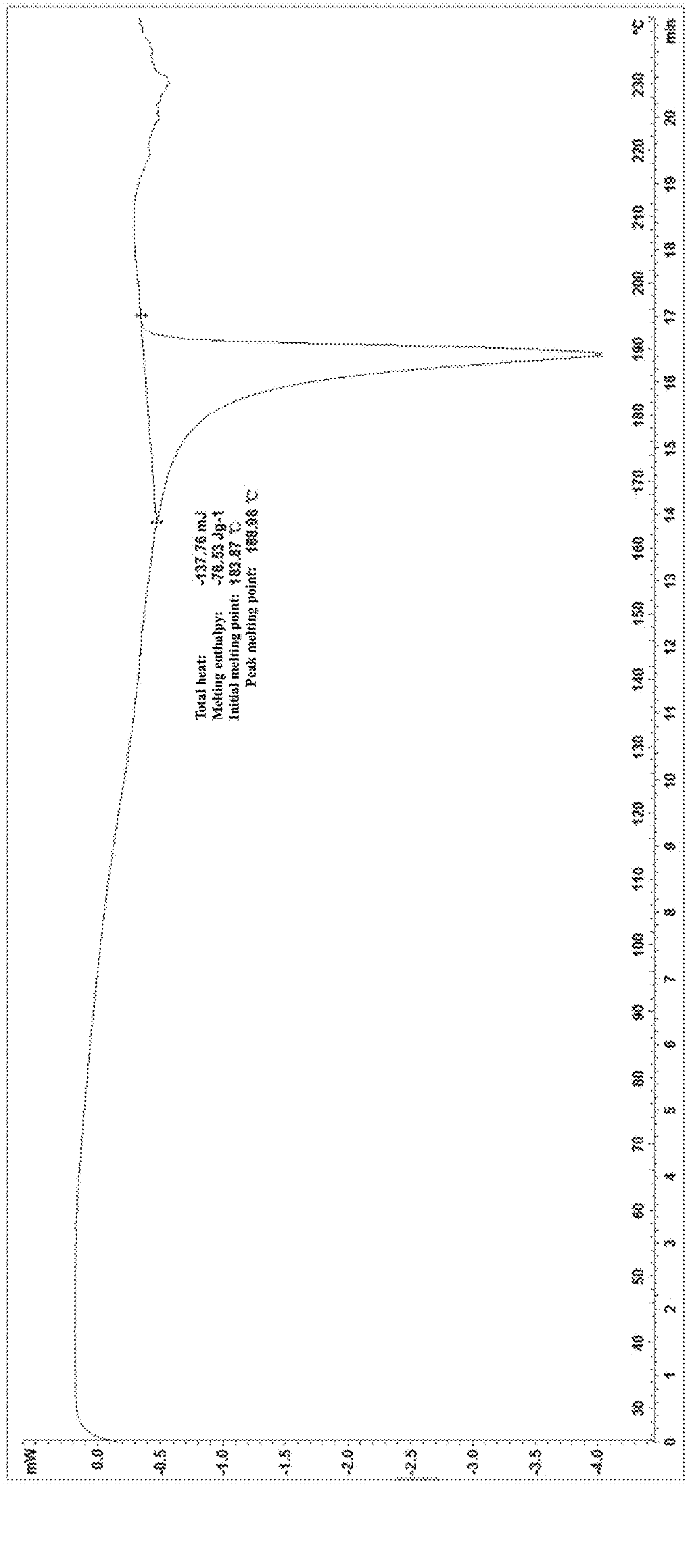
FIG. 4 shows a DSC pattern of the crystal form I of the phosphate of the compound of formula (I)
Figure 5:
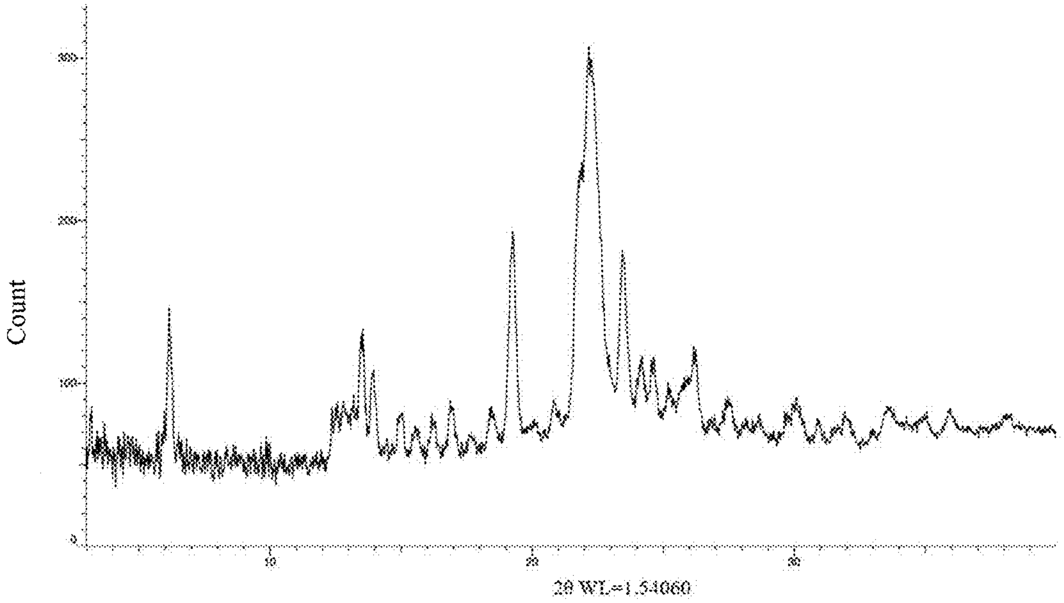
FIG. 5 shows an XRPD pattern of the crystal form I of the phosphate of the compound of formula (I) after DVS.
Figure 6:
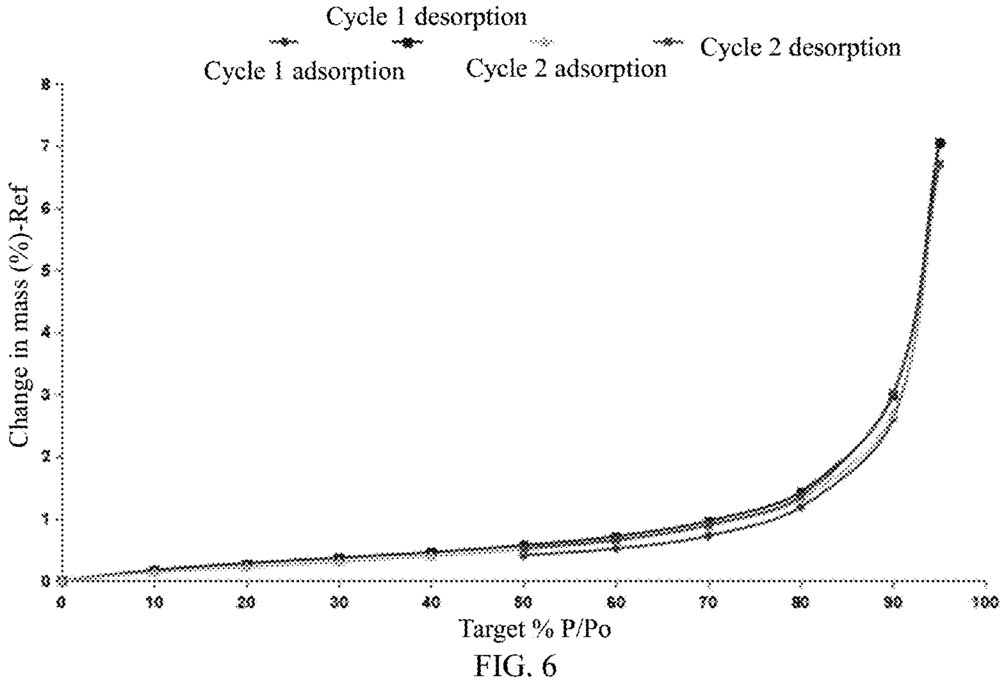
FIG. 6 shows a DVS pattern of the crystal form I of the phosphate of the compound of formula (I)
Figure 7:
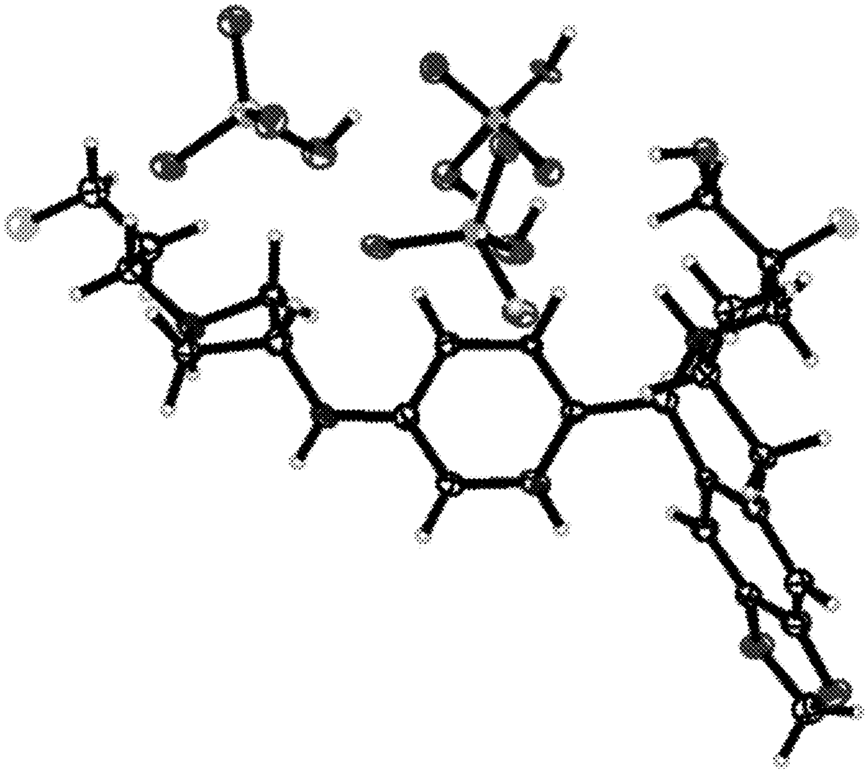
FIG. 7 shows a single crystal pattern of the crystal form I of the phosphate of the compound of formula (I)

About 450 mg of the compound of formula (I) was weighed out and dissolved in acetone (10 mL), and a solution of phosphoric acid in ethanol (1.25 mL, 1.46 M) was added. After heating and cooling for 24 h, the sample was centrifuged and dried in vacuum at 40° C. to give a solid. The solid was identified by X-ray powder diffraction as crystal form I. The XRPD pattern is shown in FIG. 2, and the characteristic peak positions are shown in Table 10. The TGA pattern (FIG. 3) shows that the crystal form I made a weight loss of 0.38% at 30-115° C.; the DSC pattern (FIG. 4) shows that the crystal form I has an endothermic peak at 188.98° C.; the XRPD pattern after DVS (FIG. 5) shows that the crystal form did not change; the DVS pattern is shown in FIG. 6; the single crystal pattern is shown in FIG. 7, wherein the free base and the phosphate radical are in a molar ratio of 1:3, and the crystal form has axial lengths a=8.0475 (3) Å; b=8.0903 (3) Å; c=84.695 (4) Å; axial angles α=89.575 (2)°; β=89.859 (2)°; γ=60.745 (2)°; and a crystal volume V=4810.7 (3) $Å^3$.

TABLE 10

Characteristic peaks of crystal form I

| Peak number | 2-θ (deg) | D (Å) | I (%) |
|---|---|---|---|
| 1 | 6.146 | 14.36866 | 100.0 |
| 2 | 12.444 | 7.10720 | 8.4 |
| 3 | 13.466 | 6.57007 | 24.1 |
| 4 | 13.922 | 6.35584 | 13.7 |
| 5 | 14.976 | 5.91087 | 8.5 |
| 6 | 16.262 | 5.44621 | 7.0 |
| 7 | 16.915 | 5.23745 | 15.0 |
| 8 | 19.222 | 4.61381 | 67.5 |
| 9 | 20.844 | 4.25832 | 7.9 |
| 10 | 21.848 | 4.06471 | 68.4 |
| 11 | 22.290 | 3.98509 | 68.2 |
| 12 | 23.436 | 3.79276 | 64.9 |
| 13 | 24.119 | 3.68697 | 9.8 |
| 14 | 24.563 | 3.62135 | 12.9 |
| 15 | 26.164 | 3.40321 | 21.6 |
| 16 | 27.475 | 3.24377 | 8.3 |
| 17 | 29.998 | 2.97638 | 16.9 |

Example 3. Preparation of Crystal Form I of Phosphate of Compound of Formula (I)

About 15 mg of the compound of formula (I) was weighed out and dissolved in ethyl acetate (0.2 mL), and a solution of phosphoric acid in ethanol (41 μL, 1.46 M) was added. After heating and cooling for 24 h, the sample was centrifuged and dried to give a solid. The solid was identified by X-ray powder diffraction as crystal form I.

Example 4. Preparation of Crystal Form A of Sulfate of Compound of Formula (I)

Figure 8:
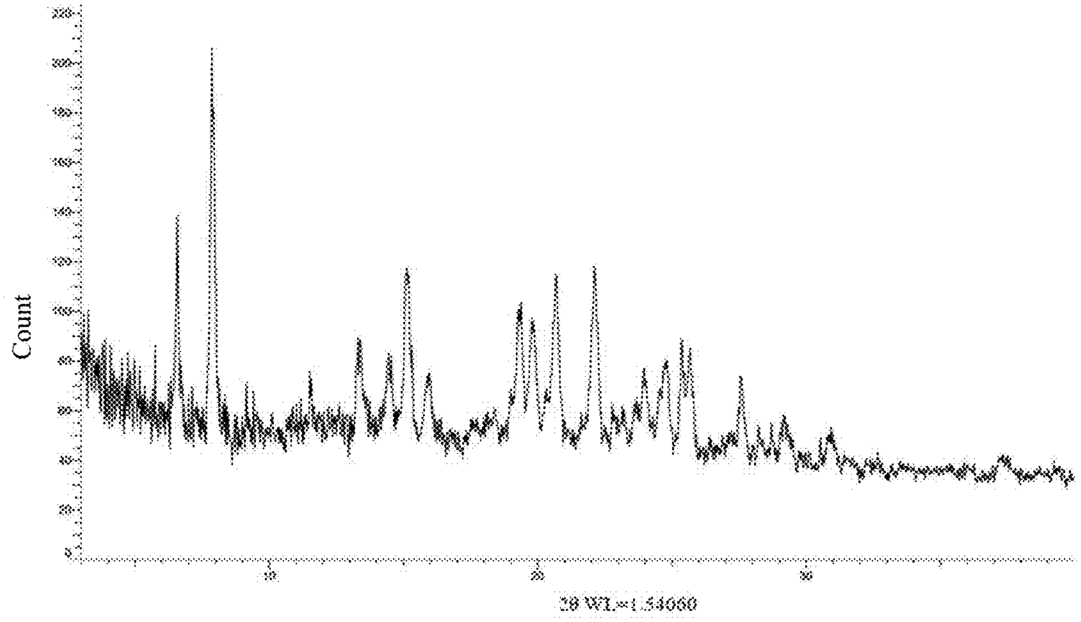
FIG. 8 shows an XRPD pattern of a crystal form A of a sulfate of the compound of formula (I)
Figure 9:
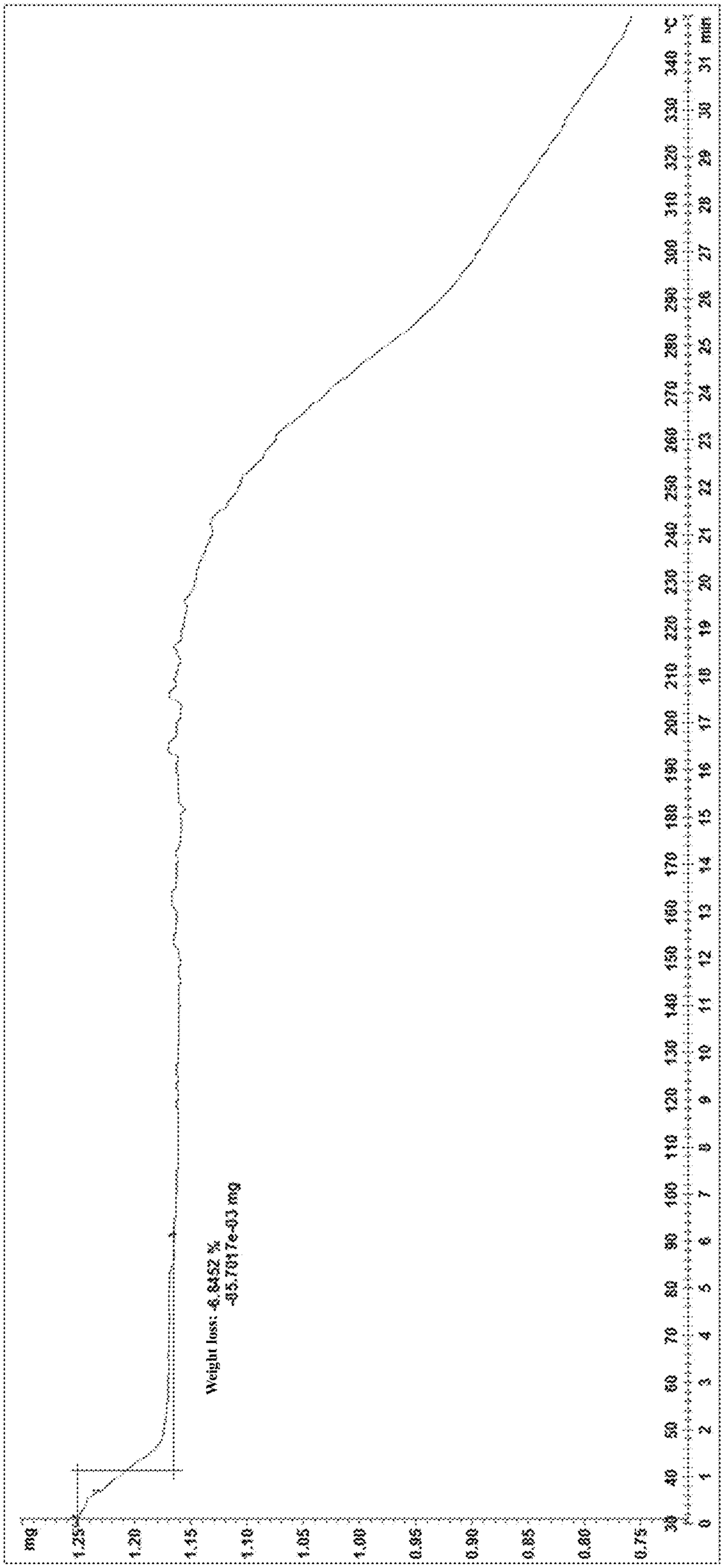
FIG. 9 shows a TGA pattern of the crystal form A of the sulfate of the compound of formula (I)
Figure 10:
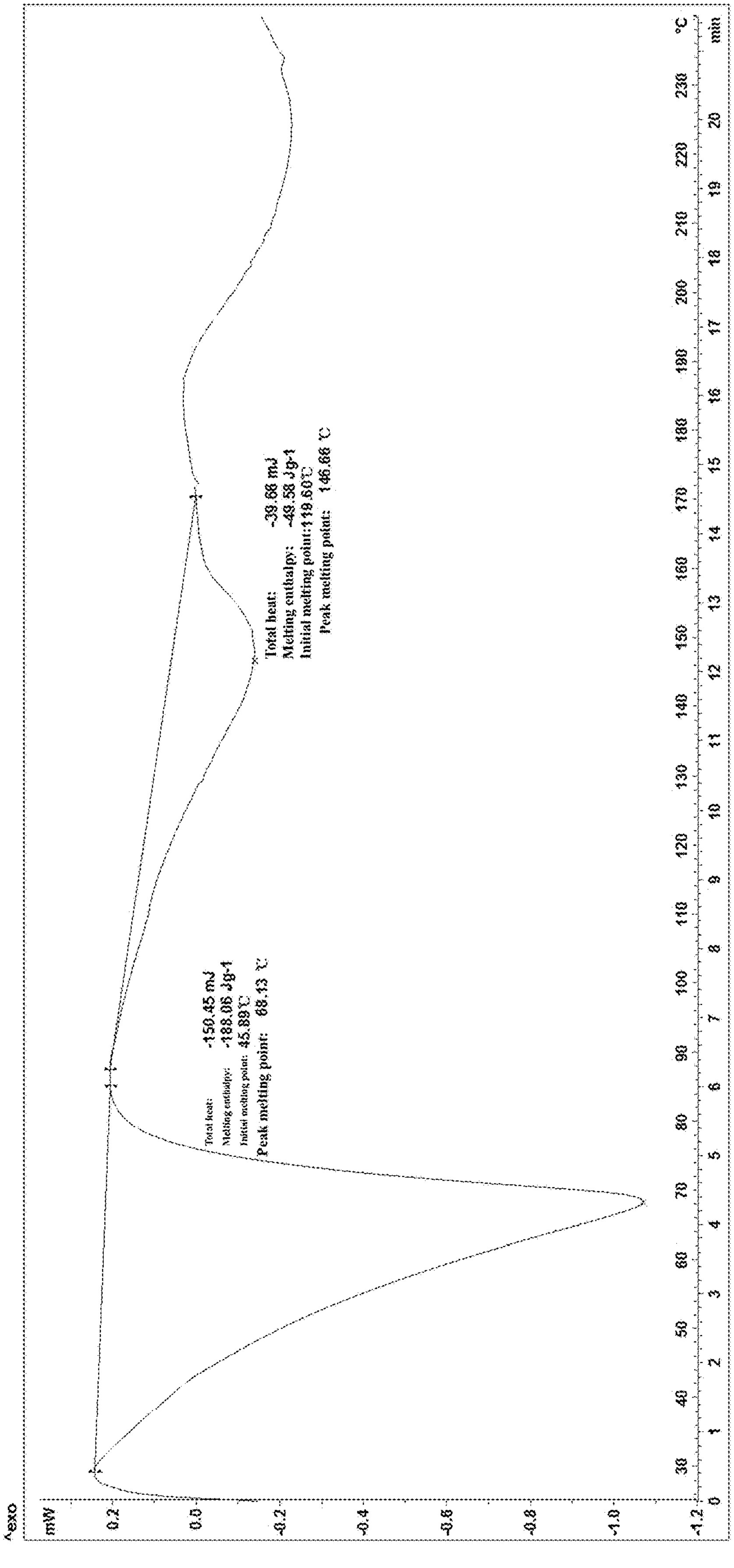
FIG. 10 shows a DSC pattern of the crystal form A of the sulfate of the compound of formula (I)
Figure 11:
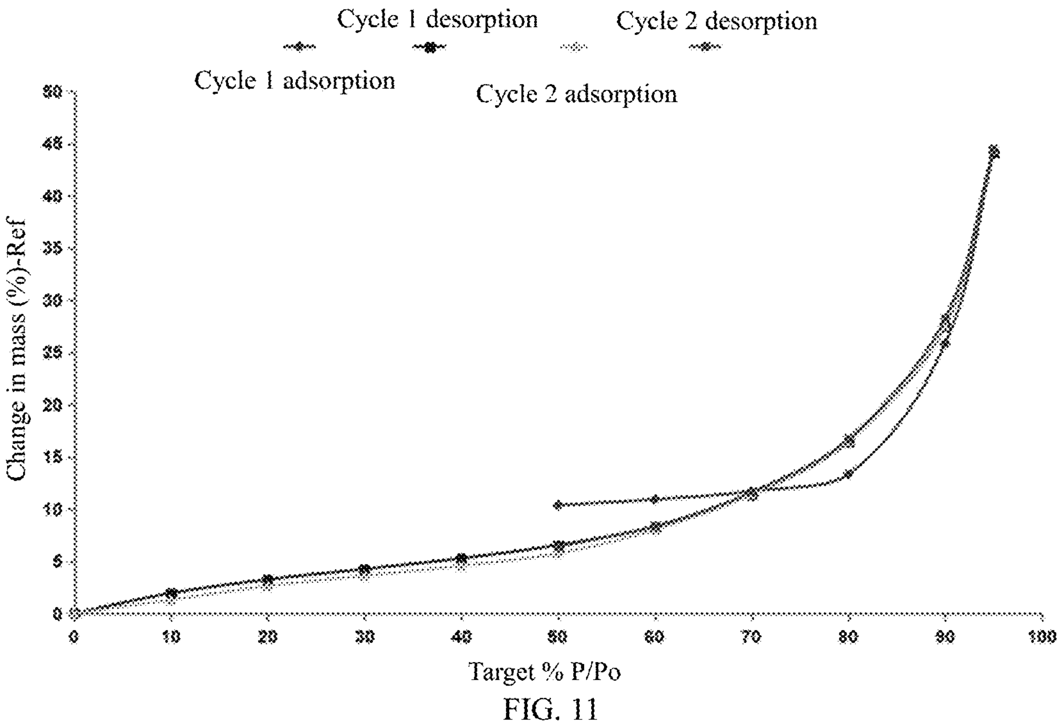
FIG. 11 shows a DVS pattern of the crystal form A of the sulfate of the compound of formula (I)
Figure 12:
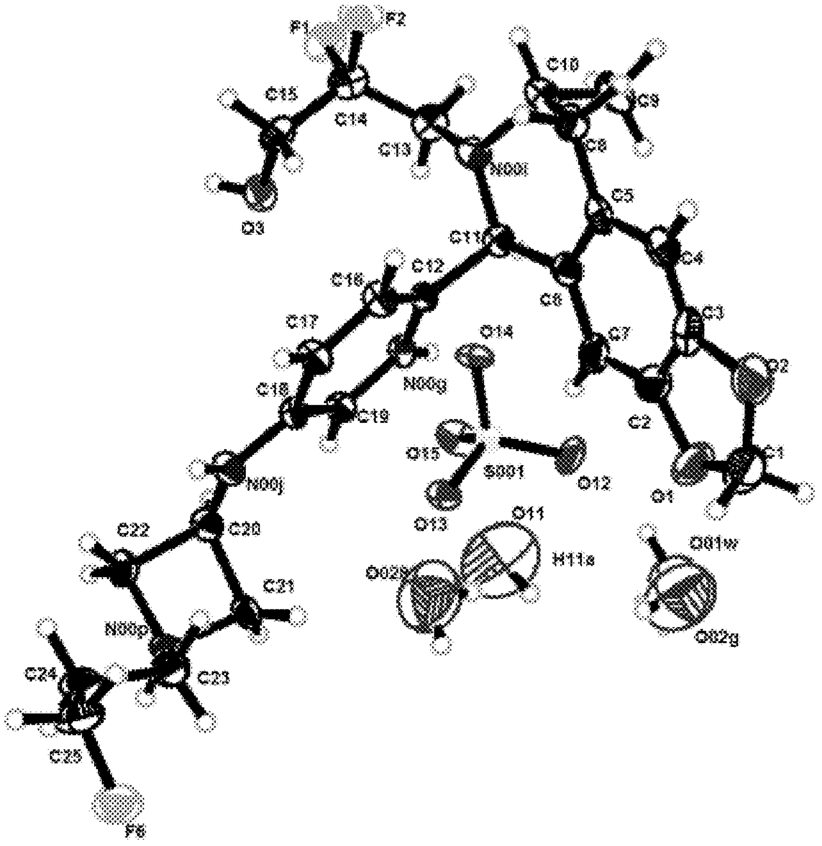
FIG. 12 shows a single crystal pattern of the crystal form A of the sulfate of the compound of formula (I)

About 15 mg of the compound of formula (I) was weighed out and dissolved in ethanol (0.2 mL), and a solution of sulfuric acid in ethanol (16.3 μL, 1.84 M) was added. After heating and cooling for 24 h, the sample was centrifuged and dried to give a solid. The solid was identified by X-ray powder diffraction as crystal form A. The XRPD pattern is shown in FIG. 8, and the characteristic peak positions are shown in Table 11. The TGA pattern (FIG. 9) shows that the crystal form A made a weight loss of 6.84% at 30-90° C.; the DSC pattern (FIG. 10) shows that the crystal form A has two endothermic peaks at 68.13° C. and 146.66° C.; the sample after DVS was deliquesced; the DVS pattern is shown in FIG. 11; the single crystal pattern is shown in FIG. 12, wherein the free base and the sulfate radical are in a molar ratio of 1:1, and the crystal form has axial lengths a=9.7051 (11) Å; b=26.208 (3) Å; c=12.1065 (13) Å; an axial angle β=90°; and a crystal volume V=3079.3 (6) $Å^3$.

TABLE 11

Characteristic peaks of crystal form A

| Peak number | 2-θ (deg) | D (Å) | I (%) |
|---|---|---|---|
| 1 | 6.582 | 13.41759 | 64.7 |
| 2 | 7.898 | 11.18575 | 100.0 |
| 3 | 11.573 | 7.64035 | 14.1 |
| 4 | 13.357 | 6.62340 | 23.2 |
| 5 | 14.469 | 6.11707 | 21.9 |
| 6 | 15.142 | 5.84641 | 49.3 |
| 7 | 15.920 | 5.56251 | 14.3 |
| 8 | 18.121 | 4.89150 | 4.6 |
| 9 | 19.335 | 4.58693 | 34.3 |
| 10 | 19.820 | 4.47579 | 28.2 |
| 11 | 20.677 | 4.29225 | 45.0 |
| 12 | 22.125 | 4.01448 | 50.5 |
| 13 | 23.980 | 3.70799 | 18.9 |
| 14 | 24.763 | 3.59249 | 23.1 |
| 15 | 25.397 | 3.50424 | 26.9 |
| 16 | 25.663 | 3.46850 | 27.8 |
| 17 | 27.200 | 3.27590 | 4.7 |
| 18 | 27.588 | 3.23072 | 21.9 |
| 19 | 28.307 | 3.15024 | 3.0 |
| 20 | 29.161 | 3.05988 | 12.0 |

Example 5. Preparation of Crystal Form A of Sulfate of Compound of Formula (I)

About 15 mg of the compound of formula (I) was weighed out and dissolved in ethyl acetate (0.2 mL), and a solution of sulfuric acid in ethanol (16.3 μL, 1.84 M) was added. After heating and cooling for 24 h, the solid was obtained by centrifugation and drying, and identified by X-ray powder diffraction as crystal form A.

Example 6. Preparation of Crystal Form A of Sulfate of Compound of Formula (I)

About 148 mg of the compound of formula (I) was weighed out and dissolved in acetone (1 mL), and a solution of sulfuric acid in ethanol (0.163 mL, 1.84 M) was added. After heating and cooling for 40 h, the solid was obtained by centrifugation and drying, and identified by X-ray powder diffraction as crystal form A.

Example 7. Preparation of Crystal Form A of Sulfate of Compound of Formula (I)

About 296 mg of the compound of formula (I) was weighed out and dissolved in methanol (1 mL), and a solution of sulfuric acid in methanol (0.33 mL, 1.84 M) was added. After heating and cooling for 24 h, the solid was obtained by centrifugation and drying, and identified by X-ray powder diffraction as crystal form A.

Example 8. Preparation of Amorphous Form of L-Tartrate of Compound of Formula (I)

Figure 13:
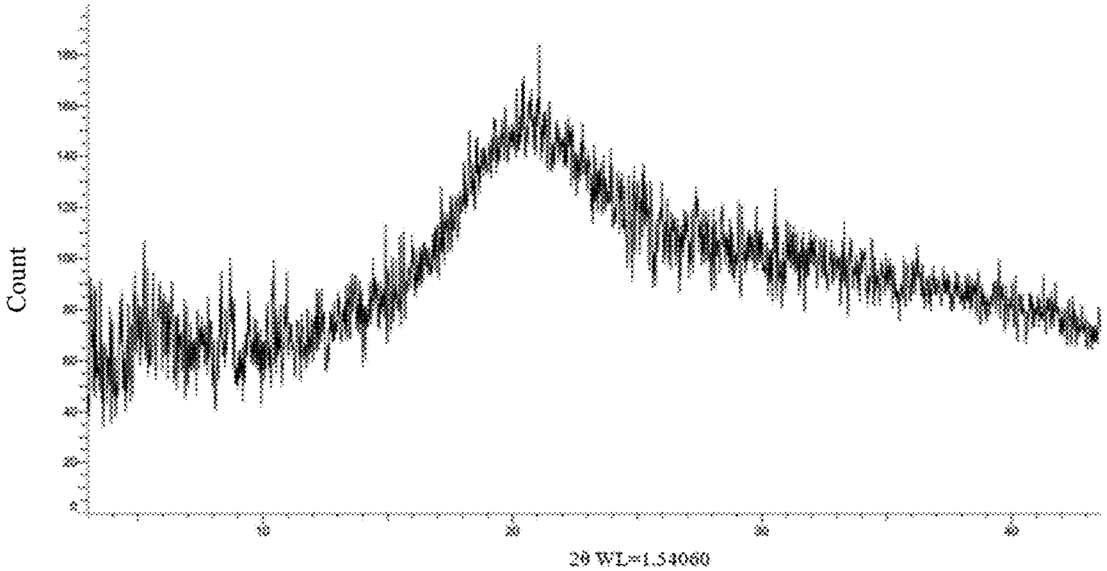
FIG. 13 shows an XRPD pattern of an amorphous form of a tartrate of the compound of formula (I)

The compound of formula (I) (25 mg) was added to isopropanol (0.5 mL), and the reaction mixture was stirred to dissolve the compound completely. L-tartaric acid (8 mg) was diluted with isopropanol (0.5 mL), and added dropwise to the above reaction solution. The mixture was stirred at room temperature in a nitrogen atmosphere to form a white turbid liquid. The turbid liquid was stirred for another 16 h and filtered. The filter cake was collected and dried in vacuum to give a white solid. The product was identified by X-ray powder diffraction as amorphous, and the XRPD pattern is shown in FIG. 13.

Example 9. Preparation of Amorphous Form of Citrate

Figure 14:
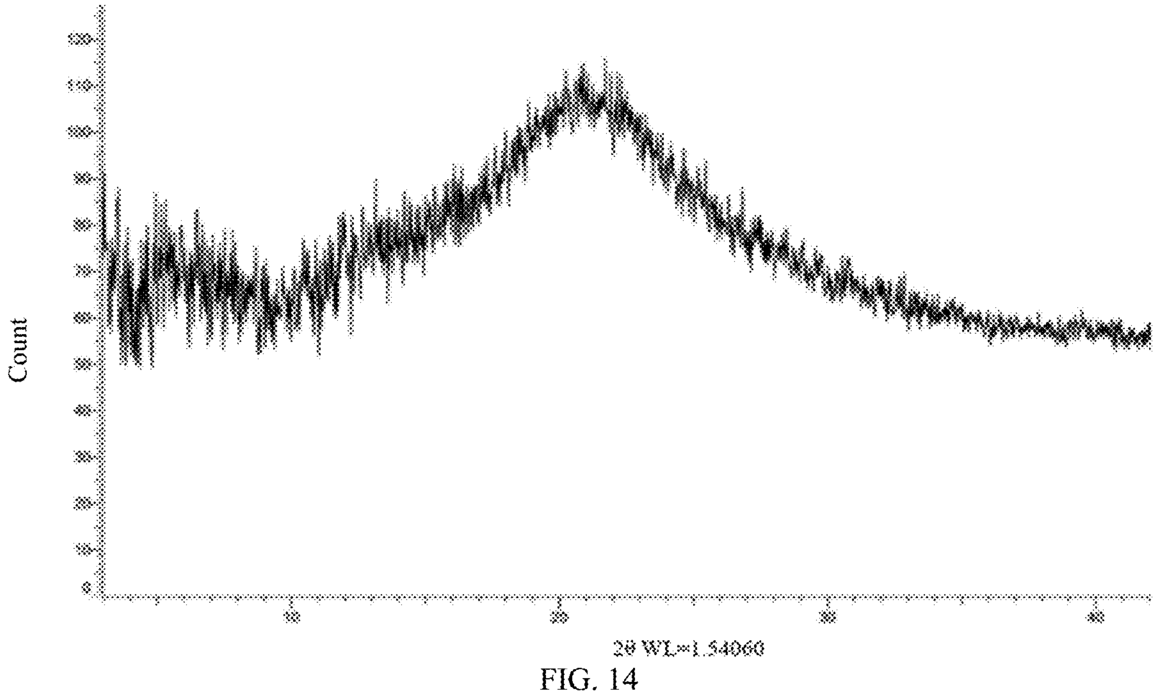
FIG. 14 shows an XRPD pattern of an amorphous form of a citrate of the compound of formula (I).

The compound of formula (I) (25 mg) was added to isopropanol (0.5 mL), and the reaction mixture was stirred to dissolve the compound completely. Citric acid (10 mg) was diluted with isopropanol (0.5 mL), and added dropwise to the above reaction solution. The mixture was stirred at room temperature in a nitrogen atmosphere to form a white turbid liquid. The turbid liquid was stirred for another 16 h and filtered. The filter cake was collected and dried in vacuum to give a white solid. The product was identified by X-ray powder diffraction as amorphous, and the XRPD pattern is shown in FIG. 14.

Example 10. Preparation of Hydrochloride

About 15 mg of the compound of formula (I) was weighed out and dissolved in ethanol (0.2 mL), and a solution of hydrochloric acid in ethanol (50 μL, 1.2 M) was added. The mixture was heated and cooled for 24 h, stirred, and volatilized at room temperature to give an oil colloidal solid.

Example 11. Preparation of Hydrobromide

About 15 mg of the compound of formula (I) was weighed out and dissolved in ethyl acetate (0.2 mL), and a solution of hydrobromic acid in ethanol (80 μL, 0.75 M) was added. The mixture was heated and cooled for 24 h, stirred, and volatilized at room temperature to give an oil colloidal solid.

Example 12. Preparation of Mesylate

About 15 mg of the compound of formula (I) was weighed out and dissolved in ethyl acetate (0.2 mL), and an aqueous solution of methanesulfonic acid (39 μL, 1.53 M) was added. The mixture was heated and cooled for 24 h, stirred, and volatilized at room temperature to give an oil colloidal solid.

Example 13. Preparation of Formate

About 15 mg of the compound of formula (I) was weighed out and dissolved in acetone (0.2 mL), and an aqueous solution of formic acid (22.6 μL, 2.65 M) was added. The mixture was heated and cooled for 24 h, stirred, and volatilized at room temperature to give an oil colloidal solid.

Example 14. Preparation of Acetate

About 15 mg of the compound of formula (I) was weighed out and dissolved in ethanol (0.2 mL), and an aqueous solution of acetic acid (34.2 μL, 1.75 M) was added. The mixture was heated and cooled for 24 h, stirred, and volatilized at room temperature to give an oil colloidal solid.

Example 15. Preparation of Succinate

About 15 mg of the compound of formula (I) was weighed out and dissolved in acetone (0.2 mL), and a solution of succinic acid in ethanol (36 μL, 0.83 M) was added. The mixture was heated and cooled for 24 h, stirred, and volatilized at room temperature to give an oil colloidal solid.

Example 16. Preparation of Maleate

About 15 mg of the compound of formula (I) was weighed out and dissolved in ethyl acetate (0.2 mL), and an aqueous solution of maleic acid (30 μL, 1 M) was added. The mixture was heated and cooled for 24 h, stirred, and volatilized at room temperature to give an oil colloidal solid.

Example 17. Preparation of Malate

About 15 mg of the compound of formula (I) was weighed out and dissolved in ethyl acetate (0.2 mL), and an aqueous solution of malic acid (30 μL, 1 M) was added. The mixture was heated and cooled for 24 h, stirred, and volatilized at room temperature to give an oil colloidal solid.

Example 18. Preparation of p-Toluenesulfonate

About 15 mg of the compound of formula (I) was weighed out and dissolved in ethanol (0.2 mL), p-toluenesulfonic acid (10.28 mg) was added, and purified water (60 μL) was added. The mixture was heated and cooled for 24 h, stirred, and volatilized at room temperature to give an oil colloidal solid.

Example 19. Hygroscopicity Study

The measurement was conducted with a Surface Measurement Systems intrinsic at 25° C., starting from 50% humidity in humidity range of 0%-95%, in steps of 10%; the criterion was dM/dT≤0.002% and TMAX of 360 min in two cycles.

TABLE 12

Hygroscopicity study data

| Test sample | 0.0% RH-95.0% RH | 0% RH-80.0% RH | Crystal form |
|---|---|---|---|
| Free amorphous form | 6.7% | 4.6% (hygroscopic) | Did not change |
| Crystal form I of phosphate | 7.1% | 1.2% (slightly hygroscopic) | Did not change |
| Crystal form A of sulfate | 44.1% | 13.3% (hygroscopic) | Deliquescence |

Example 20. Influencing Factor Stability Study

The free amorphous form, the crystal form I of the phosphate and the crystal form A of the sulfate were left to stand open, and their stability under a lighting condition (4500 Lux), high-temperature conditions (40° C. and 60° C.), high-humidity conditions (75% RH and 92.5% RH) was investigated in a period of 30 days.

TABLE 13

Result of a 30-day influencing factor test for 1 month

| Conditions | Time | Free amorphous form | |
|---|---|---|---|
| | | Purity (%) | Crystal form |
| Initial | 0 days | 97.1 | Amorphous form |
| 40° C. | 5 days | 96.7 | Amorphous form |
| | 10 days | 96.5 | Amorphous form |
| | 1 month | 95.4 | Amorphous form |

TABLE 13-continued

| Result of a 30-day influencing factor test for 1 month | | | |
|---|---|---|---|
| 60° C. | 5 days | 95.7 | Amorphous form |
| | 10 days | 94.2 | Amorphous form |
| | 1 month | 87.6 | Amorphous form |
| 4500 Lux | 5 days | 94.0 | Amorphous form |
| | 10 days | 89.9 | Amorphous form |
| | 1 month | 71.7 | Amorphous form |
| 75% RH | 5 days | 97.0 | Amorphous form |
| | 10 days | 97.0 | Amorphous form |
| | 1 month | 96.9 | Deliquescence |
| 92.5% RH | 5 days | 96.9 | Amorphous form |
| | 10 days | 97.0 | Amorphous form |
| | 1 month | 97.0 | Deliquescence |
| | | Crystal form I of phosphate | |
| Conditions | Time (days) | Purity (%) | Crystal form |
| Initial | 0 | 99.4 | Crystal form I |
| 40° C. | 5 days | 99.3 | Crystal form I |
| | 10 days | 99.1 | Crystal form I |
| | 1 month | 99.1 | Crystal form I |
| 60° C. | 5 days | 99.1 | Crystal form I |
| | 10 days | 99.1 | Crystal form I |
| | 1 month | 98.8 | Crystal form I |

TABLE 13-continued

| Result of a 30-day influencing factor test for 1 month | | | |
|---|---|---|---|
| 4500 Lux | 5 days | 98.9 | Crystal form I |
| | 10 days | 98.8 | Crystal form I |
| | 1 month | 98.4 | Crystal form I |
| 75% RH | 5 days | 99.3 | Crystal form I |
| | 10 days | 99.4 | Crystal form I |
| | 1 month | 99.4 | Crystal form I |
| 92.5% RH | 5 days | 99.3 | Crystal form I |
| | 10 days | 99.3 | Crystal form I |
| | 1 month | 99.3 | Crystal form I |
| | | Crystal form A of sulfate | |
| Conditions | Time (days) | Purity (%) | Crystal form |
| Initial | 0 | 98.9 | Crystal form A |
| 40° C. | 5 days | 98.8 | Crystal form A |
| | 10 days | 98.7 | Crystal form A |
| | 1 month | 98.0 | Crystal form A |
| 60° C. | 5 days | 98.7 | Crystal form A |
| | 10 days | 98.6 | Crystal form A |
| | 1 month | 97.3 | Crystal form A |
| 4500 Lux | 5 days | 97.4 | Crystal form A |
| | 10 days | 96.0 | Crystal form A |
| | 1 month | 92.9 | Crystal form A |
| 75% RH | 5 days | 97.8 | Deliquescence |
| | 10 days | 96.6 | Deliquescence |
| | 1 month | 94.8 | Deliquescence |
| 92.5% RH | 5 days | 98.1 | Deliquescence |
| | 10 days | 97.3 | Deliquescence |
| | 1 month | 95.1 | Deliquescence |

Conclusion: The influencing factor study showed that: the crystal form I of the phosphate has good physical and chemical stability after being placed for 30 days under the conditions of the influencing factors. The crystal form A of the sulfate has good physical and chemical stability under other conditions except the lighting condition, and is deliquesced under the high-humidity conditions. The amorphous form is deliquesced under the high-humidity conditions, has physical stability under other conditions, and has poor chemical stability under the high-temperature conditions and the lighting condition.

Experimental Example 21. Long-Term/Accelerated Stability

The free amorphous form, the crystal form I of the phosphate and the crystal form A of the sulfate were placed under the conditions of 25° C./60% RH and 40° C./75% RH to investigate their stability:

TABLE 14

| Long-term/accelerated stability of free amorphous base | | | | | | | |
|---|---|---|---|---|---|---|---|
| Placement conditions | Purity (%) Initial | Purity (%) 7 days | Purity (%) 14 days | Purity (%) 1 month | Purity (%) 2 months | Purity (%) 3 months | Crystal form 3 months |
| 25° C./60% RH | 97.1 | 97.1 | 97.0 | 97.1 | 96.7 | 96.7 | Unchanged |
| 40° C./75% RH | 97.1 | 96.8 | 96.6 | 96.5 | 95.5 | 94.9 | Unchanged |

TABLE 15

| Long-term/accelerated stability of crystal form I of phosphate | | | | | | | |
|---|---|---|---|---|---|---|---|
| Placement conditions | Purity (%) Initial | Purity (%) 7 days | Purity (%) 14 days | Purity (%) 1 month | Purity (%) 2 months | Purity (%) 3 months | Crystal form |
| 25° C./60% RH | 99.4 | 99.4 | 99.5 | 99.3 | 99.3 | 99.2 | Unchanged |
| 40° C./75% RH | 99.4 | 99.5 | 99.5 | 99.3 | 99.2 | 99.0 | Unchanged |

TABLE 16

| Long-term/accelerated stability of crystal form A of sulfate | | | | | | | |
|---|---|---|---|---|---|---|---|
| Placement conditions | Purity (%) Initial | Purity (%) 7 days | Purity (%) 14 days | Purity (%) 1 month | Purity (%) 2 months | Purity (%) 3 months | Crystal form |
| 25° C./60% RH | 98.9 | 99.0 | 98.9 | 98.9 | 98.7 | 98.8 | Unchanged |
| 40° C./75% RH | 98.9 | 99.2 | 98.9 | 98.7 | 98.2 | 98.1 | Unchanged |

Conclusion: The stability results after the long-term/accelerated study for 3 months showed that the crystal form I of the phosphate and the crystal form A of the sulfate have good physical and chemical stability, which is slightly superior to that of the free amorphous form.

The invention claimed is:

1. A pharmaceutically acceptable salt of a compound of formula (I), wherein the pharmaceutically acceptable salt is selected from the group consisting of phosphate, sulfate, tartrate, citrate, hydrochloride, hydrobromide, mesylate, formate, acetate, succinate, maleate, malate, and p-toluenesulfonate, (I)

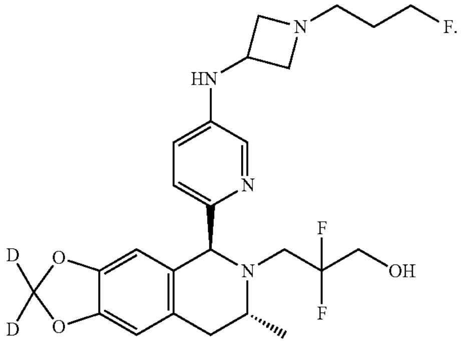

2. The pharmaceutically acceptable salt of the compound of formula (I) according to claim 1, wherein the compound of formula (I) and an acid molecule are in an amount-of-substance ratio selected from the group consisting of 5:1 to 1:5.

3. The pharmaceutically acceptable salt of the compound of formula (I) according to claim 2, being a phosphate, wherein the compound of formula (I) and a phosphoric acid molecule are in an amount-of-substance ratio of 1:3.

4. A crystal form I of a phosphate of a compound of formula (I) according to claim 3, wherein the compound of formula (I) and a phosphoric acid molecule are in an amount-of-substance ratio of 1:3, and in an X-ray powder diffraction pattern, the crystal form has characteristic peaks at 2θ angles of diffraction of 6.1, 13.5, 19.2, and 22.3, (I)

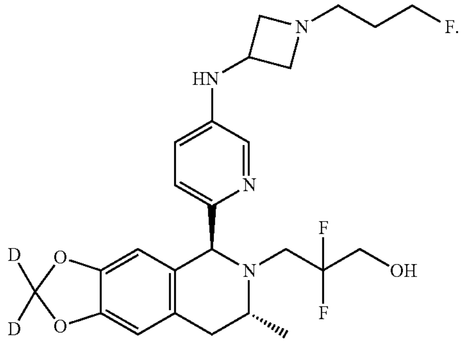

wherein the 2θ angles have a margin of error of ±0.2.

5. The pharmaceutically acceptable salt of the compound of formula (I) according to claim 2, being a sulfate, wherein the compound of formula (I) and a sulfuric acid molecule are in an amount-of-substance ratio of 1:1.

6. A crystal form A of a sulfate of a compound of formula (I) according to claim 5, wherein the compound of formula (I) and a sulfuric acid molecule are in an amount-of-substance ratio of 1:1, and in an X-ray powder diffraction pattern, the crystal form has characteristic peaks at 2θ angles of diffraction of 6.6, 7.9, 15.1, 20.7, and 22.1, (I)

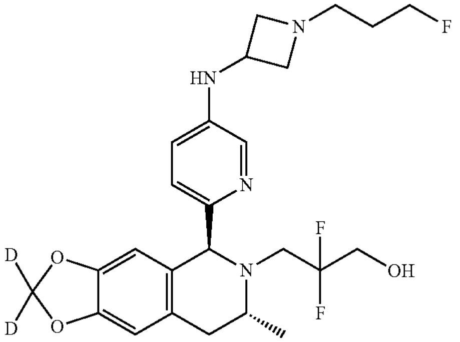

wherein the 2θ angles have a margin of error of ±0.2.

7. A method for preparing the pharmaceutically acceptable salt of the compound of formula (I) according to claim 3, wherein the pharmaceutically acceptable salt is a phosphate, and the method comprises the step of reacting the compound of formula (I) with phosphoric acid.

8. A method for preparing the crystal form I of the phosphate of the compound of formula (I) according to claim 4, comprising the following steps:

1) preparing a solution of the compound of formula (I) in a solvent A, wherein the solvent A is selected from the group consisting of a ketone solvent, an ester solvent, and an ether solvent;
2) preparing a solution of phosphoric acid in a solvent B, wherein the solvent B is selected from the group consisting of water and an alcohol solvent; and
3) mixing the solution of the compound of formula (I) in the solvent A and the solution of phosphoric acid in the solvent B and then performing crystallization.

9. A method for preparing the crystal form A of the sulfate of the compound of formula (I) according to claim 6, comprising the following steps:

1) preparing a solution of the compound of formula (I) in a solvent A, wherein the solvent A is selected from the group consisting of a ketone solvent, an ester solvent, a nitrile solvent, and an alcohol solvent; the solvent A is preferably acetone, ethyl acetate, acetonitrile, methanol, or ethanol;
2) preparing a solution of sulfuric acid in a solvent B, wherein the solvent B is selected from the group consisting of water, a nitrile solvent, and an alcohol solvent; and
3) mixing the solution of the compound of formula (I) in the solvent A and the solution of sulfuric acid in the solvent B and then performing crystallization.

10. A method for preparing the pharmaceutically acceptable salt of the compound of formula (I) according to claim 1, comprising the step of reacting the compound of formula (I) with sulfuric acid, tartaric acid, citric acid, hydrochloric acid, hydrobromic acid, methanesulphonic acid, formic acid, acetic acid, succinic acid, maleic acid, malic acid, or p-toluenesulfonic acid to form a salt.

11. A pharmaceutical composition comprising the following ingredients:

1) the pharmaceutically acceptable salt of the compound of formula (I) according to claim 1; and
2) optional pharmaceutically acceptable carriers, diluents, or excipients.

12. A method for preparing a pharmaceutical composition comprising the step of mixing 1) the pharmaceutically acceptable salt of the compound of formula (I) according to claim 1; and
2) optional pharmaceutically acceptable carriers, diluents, or excipients.

13. A method for modulating estrogen receptor in a patient in need thereof, comprising: administering to the patient a therapeutically effective amount of the pharmaceutically acceptable salt of the compound of formula (I) according to claim 1.

14. A method for preventing and/or treating cancer in a patient in need thereof, comprising: administering to the patient a therapeutically effective amount of the pharmaceutically acceptable salt of the compound of formula (I) according to claim 1.

15. A method for preventing and/or treating an estrogen receptor-mediated or -dependent disease or condition in a patient in need thereof, comprising: administering to the patient a therapeutically effective amount of the pharmaceutically acceptable salt of the compound of formula (I) according to claim 1.

16. A method for selective degrading estrogen receptor in a patient in need thereof, comprising: administering to the patient a therapeutically effective amount of the pharmaceutically acceptable salt of the compound of formula (I) according to claim 1.

17. The crystal form I of a phosphate of a compound of formula (I) according to claim 3, in the X-ray powder diffraction pattern, the crystal form has characteristic peaks at 2θ angles of diffraction of 6.1, 13.5, 13.9, 19.2, 21.8, 22.3, and 23.4, wherein the 2θ angles have a margin of error of ±0.2.

18. The crystal form I of a phosphate of a compound of formula (I) according to claim 3, in the X-ray powder diffraction pattern, the crystal form has characteristic peaks at 2θ angles of diffraction of 6.1, 12.4, 13.5, 13.9, 15.0, 16.3, 16.9, 19.2, 20.8, 21.8, 22.3, 23.4, 24.1, 24.6, 26.2, 27.5, and 30.0, wherein the 2θ angles have a margin of error of ±0.2.

19. The crystal form A of a sulfate of a compound of formula (I) according to claim 5, in the X-ray powder diffraction pattern, the crystal form has characteristic peaks at 2θ angles of diffraction of 6.6, 7.9, 13.4, 14.5, 15.1, 19.3, 19.8, 20.7, 22.1, 24.8, 25.4, 25.7, and 27.6, wherein the 2θ angles have a margin of error of ±0.2.

20. The crystal form A of a sulfate of a compound of formula (I) according to claim 5, in the X-ray powder diffraction pattern, the crystal form has characteristic peaks at 2θ angles of diffraction of 6.6, 7.9, 11.6, 13.4, 14.5, 15.1, 15.9, 18.1, 19.3, 19.8, 20.7, 22.1, 24.0, 24.8, 25.4, 25.7, 27.2, 27.6, 28.3, and 29.2, wherein the 2θ angles have a margin of error of ±0.2.

21. The method for preparing the crystal form I of the phosphate of the compound of formula (I) according to claim 4, comprising the following steps:

1) preparing a solution of the compound of formula (I) in a solvent A, wherein the solvent A is selected from the group consisting of acetone, ethyl acetate, or methyl tert-butyl ether;
2) preparing a solution of phosphoric acid in a solvent B, wherein the solvent B is selected from the group consisting of methanol, ethanol, or water; and
3) mixing the solution of the compound of formula (I) in the solvent A and the solution of phosphoric acid in the solvent B and then performing crystallization.

22. The method for preparing the crystal form A of the sulfate of the compound of formula (I) according to claim 6, comprising the following steps:

1) preparing a solution of the compound of formula (I) in a solvent A, wherein the solvent A is selected from the group consisting of acetone, ethyl acetate, acetonitrile, methanol, or ethanol;
2) preparing a solution of sulfuric acid in a solvent B, wherein the solvent B is selected from the group consisting methanol, ethanol, water, or acetonitrile; and
3) mixing the solution of the compound of formula (I) in the solvent A and the solution of sulfuric acid in the solvent B and then performing crystallization.

23. The method for preventing and/or treating cancer in a patient in need thereof according to claim 14, wherein the cancer is selected from the group consisting of breast cancer, endometrial cancer, uterine cancer, cervical cancer, skin cancer, prostate cancer, ovarian cancer, fallopian tube tumor, hemophilia, and leukemia.

24. The method for preventing and/or treating an estrogen receptor-mediated or -dependent disease or condition in a patient in need thereof according to claim 15, wherein the estrogen receptor-mediated or -dependent disease or condition is selected from the group consisting of cancer, central nervous system deficit, cardiovascular system deficit, blood system deficit, immune and inflammatory disease, susceptible infection, metabolic deficit, neurologic deficit, psychiatric deficit, and reproductive deficit.

25. The method for preventing and/or treating an estrogen receptor-mediated or -dependent disease or condition in a patient in need thereof according to claim 24, wherein the cancer is selected from the group consisting of breast cancer, endometrial cancer, uterine cancer, cervical cancer, skin cancer, prostate cancer, ovarian cancer, fallopian tube tumor, hemophilia, and leukemia.

26. The method for preventing and/or treating an estrogen receptor-mediated or -dependent disease or condition in a patient in need thereof according to claim 25, wherein the cancer is selected from the group consisting of breast cancer, ovarian cancer, endometrial cancer, prostate cancer, and uterine cancer.

* * * * *

SEQUENCE LISTING

```
Sequence total quantity: 2
SEQ ID NO: 1            moltype = DNA  length = 39
FEATURE                 Location/Qualifiers
source                  1..39
                        mol_type = other DNA
                        note = Y537S
                        organism = synthetic construct
SEQUENCE: 1
aagaacgtgg tgcccctctc tgacctgctg ctggagatg                  39

SEQ ID NO: 2            moltype = DNA  length = 39
FEATURE                 Location/Qualifiers
source                  1..39
                        mol_type = other DNA
                        note = Y537S
                        organism = synthetic construct
SEQUENCE: 2
catctccagc agcaggtcag agaggggcac cacgttctt                  39
```